United States Patent
Mansfield et al.

(10) Patent No.: US 8,088,927 B2
(45) Date of Patent: Jan. 3, 2012

(54) FUNGICIDE N-CYCLOALKYL-BENZYL-AMIDE DERIVATIVES

(75) Inventors: Darren Mansfield, Kürten (DE); Pierre-Yves Coqueron, Lyons (FR); Philippe Desbordes, Lyons (FR); Alain Villier, Collonges au Mont d'Or (FR); Marie-Claire Grosjean-Cournoyer, Curis au Mont d'Or (FR); Stéphanie Gary, Champagne au Mont d'Or (FR); Stéphane Carbonne, Lyons (FR); Ralf Dunkel, Lyons (FR); Arounarith Tuch, Lyons (FR); Jean-Pierre Vors, Sainte Foy les Lyon (FR)

(73) Assignee: Bayer Cropscience AG (DE)

( * ) Notice: Subject to any disclaimer, the term of this patent is extended or adjusted under 35 U.S.C. 154(b) by 658 days.

(21) Appl. No.: 12/223,105

(22) PCT Filed: Nov. 15, 2006

(86) PCT No.: PCT/EP2006/068478
§ 371 (c)(1),
(2), (4) Date: Jul. 21, 2008

(87) PCT Pub. No.: WO2007/087906
PCT Pub. Date: Aug. 9, 2007

(65) Prior Publication Data
US 2010/0286221 A1    Nov. 11, 2010

(30) Foreign Application Priority Data
Feb. 1, 2006 (EP) ..................... 06356008

(51) Int. Cl.
*C07D 291/00* (2006.01)
*C07D 419/00* (2006.01)
*C07D 515/00* (2006.01)
*C07D 285/06* (2006.01)

(52) U.S. Cl. ....................... 548/122; 548/127

(58) Field of Classification Search .................. 548/122, 548/127
See application file for complete search history.

(56) References Cited

U.S. PATENT DOCUMENTS
4,177,054 A    12/1979 Arndt et al.
4,314,839 A    2/1982 Kruger et al.

FOREIGN PATENT DOCUMENTS
JP    04 128275    4/1992

OTHER PUBLICATIONS

Nicolaou, K. C. et al: "Natural Product-like Combinatorial Libraries Based on Privileged Structures. 2. Construction of a 10 OOO-Membered Benzopyran Library by Directed Split-and-Pool Chemistry Using NanoKans and Optical Encoding" Journal of the American Chemical Society, 122(41),9954-9967 CODEN: JACSAT; ISSN: 0002-7863, 2000, XP002386053.
Hone, Neal D. et al: "A highly acid labile silicon linker for solid phase synthesis" Tetrahedron Letters, 39(8), 897-900 CODEN: TELEAY; ISSN: 0040-4039, 1998, XP004834157.
Database Chemcats [Online] chemical abstract service, retrieved from STN; XP002386056 Database accession No. 2005:638460 order No. OR24778 CAS RN: 649573-01-3 & "Apollo scientific intermediates product list" Sep. 23, 2005, Apollo Scientific LTD, Bredbury, Stockport, Cheshire SK6 2QR, United Kingdom.
Database Chemcats chemical abstract service, retrieved from STN; XP002386057 order No. T5493382, CAS RN : 875444-78-3, order No. T5464984, CAS RN: 873872-61-8 & "enamine screening library" Jan. 24, 2006, ENAMIN, Kiev, 01103, Ukraine.
Neal D. Hone et al., "A Highly Acid Labile Silicon Linger for Solid Phase Synthesis," 39(8) Tetrahedron Letters 897-900 (Feb. 19, 1998).
K.C. Nicolaou et al., "Natural Product-like Combinatorial Libraries Based on Privileged Structures," 122(41) J. Am. Chem Soc. 9954-67 (Oct. 18, 2000).
Chemical Abstract Service Registry No. 649573-01-3, "2-Furancarboxamide, N-[5-methyl-2-(1-methylethyl)cyclohexyl]-N-(phenylmethyl)-," entered STN Feb. 12, 2004, Maybridge PLC.
Chemical Abstract Service Registry No. 875444-78-3, "2-Furancarboxamide, N-(1,3-benzodioxol-5-ylmethyl)-N-cyclopentyl-5-methyl-," entered STN Feb. 28, 2006, Enamine.
Chemical Abstract Service Registry No. 873872-61-8, "3-Furancarboxamide, N-(1,3-benzodioxol-5-ylmethyl)-N-cyclopentyl-2, 5-dimethyl-," entered STN Feb. 9, 2006, Enamine.

*Primary Examiner* — San-Ming Hui
*Assistant Examiner* — Kathrien Cruz
(74) *Attorney, Agent, or Firm* — Ostrolenk Faber LLP

(57) ABSTRACT

The present invention relates to N-cycloalkyl-benzyl-amide derivatives of formula (I) wherein the substituents are as in the description, their process of preparation, their use as fungicide active agents, particularly in the form of fungicide compositions, and methods for the control of phytopathogenic fungi, notably of plants, using these compounds or compositions:

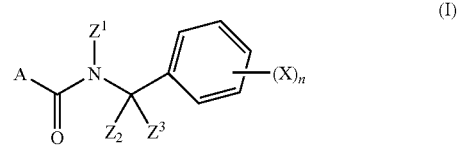

16 Claims, 1 Drawing Sheet

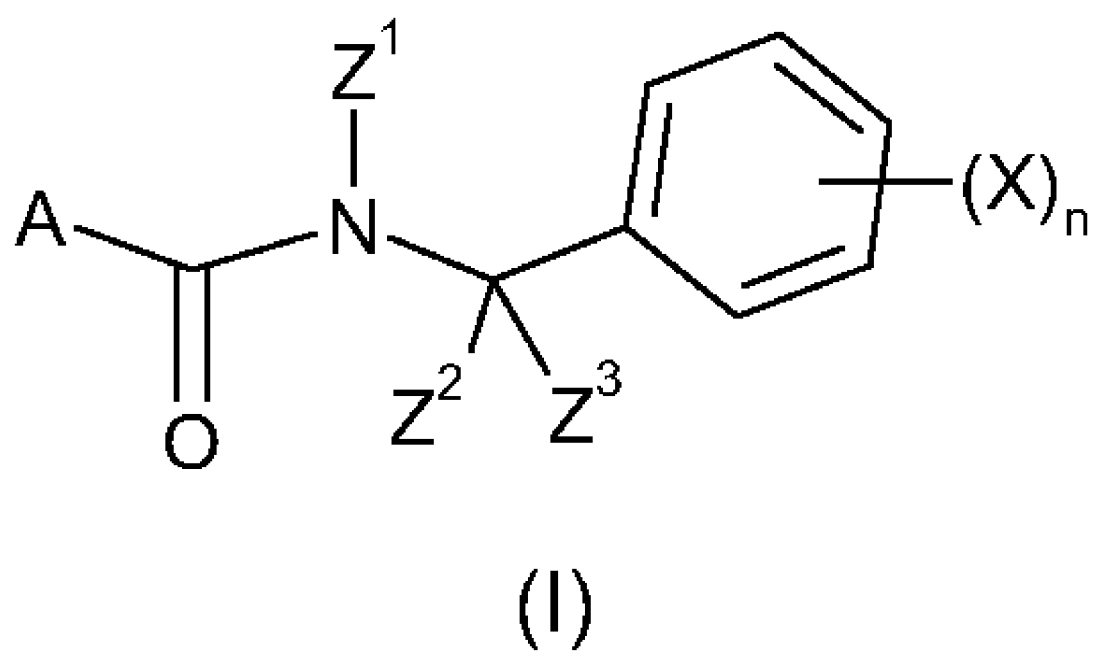
(I)

FUNGICIDE N-CYCLOALKYL-BENZYL-AMIDE DERIVATIVES

CROSS REFERENCE TO RELATED APPLICATION(S)

The present application is a 35 U.S.C. §371 national phase conversion of International Application No. PCT/EP2006/068478 filed 15 Nov. 2006, which claims priority of European Application No. 06356008.0 filed 1 Feb. 2006.

The present invention relates to N-cycloalkyl-benzyl-amide derivatives, their process of preparation, their use as fungicide active agents, particularly in the form of fungicide compositions, and methods for the control of phytopathogenic fungi, notably of plants, using these compounds or compositions.

U.S. Pat. No. 4,314,839 generically discloses 1,2,3-methyl-thiadiazole-5-carboxylic acid amide derivatives that can include a phenyl group and wherein the nitrogen atom can be substituted by a cyclohexyl group. These compounds largely differ from the compounds according to the invention, either in their chemical structure or in their properties.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds.

We have now found a new family of compounds which possess the above mentioned effects or advantages.

Accordingly, the present invention provides N-cycloalkyl-benzyl-amide derivatives of formula (I):

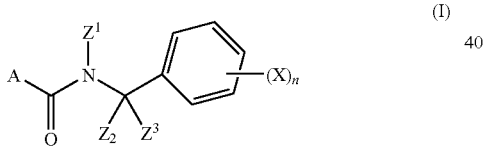

(I)

wherein
  A represents a carbo-linked, unsaturated, 5-membered heterocyclyl group that can be substituted by up to four groups R;
  Z1 represents a non substituted C3-C7-cycloalkyl or a C3-C7 cycloalkyl substituted by up to 10 atoms or groups which can be the same or different and which can be selected in the list consisting of halogen atoms; cyano; C1-C8-alkyl; C1-C8-halogenoalkyl comprising up to 9 halogen atoms which can be the same or different; C1-C8-alkoxy; C1-C8-halogenoalkoxy comprising up to 9 halogen atoms which can be the same or different; C1-C8-alkoxycarbonyl; C1-C8-halogenoalkoxycarbonyl comprising up to 9 halogen atoms which can be the same or different; C1-C8-alkylaminocarbonyl; di-C1-C8-alkylaminocarbonyl;
  $Z^2$ and $Z^3$, which can be the same or different, represent a hydrogen atom; $C_1$-$C_8$-alkyl; $C_2$-$C_8$-alkenyl; $C_2$-$C_8$-alkynyl; cyano; nitro; a halogen atom; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbamoyl; di-$C_1$-$C_8$-alkylcarbamoyl; N—$C_1$-$C_8$-alkyl-$C_1$-$C_8$-alkoxycarbamoyl; or
  $Z^2$ and $Z^3$ together with the carbon atom to which they are linked can form a substituted or non substituted $C_3$-$C_7$ cycloalkyl;
  X, which can be the same or different, represents a halogen atom; nitro; cyano; hydroxyl; sulfanyl; amino; pentafluoro-λ6-sulfanyl; $C_1$-$C_8$-alkyl; $C_1$-$C_8$-halogenoalkyl comprising up to 9 halogen atoms which can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; $C_1$-$C_8$-alkylsulfanyl; $C_1$-$C_8$-halogenoalkylsulfanyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different $C_2$-$C_8$-alkenyloxy; $C_2$-$C_8$-halogenoalkenyloxy comprising up to 9 halogen atoms which can be the same or different; $C_2$-$C_8$-alkinyloxy; $C_2$-$C_8$-halogenoalkinyloxy comprising up to 9 halogen atoms which can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms which can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms which can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl; $C_1$-$C_8$-alkylcarbonyloxy; $C_1$-$C_8$-halogenoalkylcarbonyloxy comprising up to 9 halogen atoms which can be the same or different; $C_1$-$C_8$-alkylcarbonylamino; $C_1$-$C_8$-halogenoalkylcarbonylamino comprising up to 9 halogen atoms which can be the same or different; $C_1$-$C_8$-alkylaminocarbonyloxy; di-$C_1$-$C_8$-alkylaminocarbonyloxy; $C_1$-$C_8$-alkyloxycarbonyloxy, $C_1$-$C_8$-alkylsulphenyl, $C_1$-$C_8$-halogenoalkylsulphenyl comprising up to 9 halogen atoms which can be the same or different, $C_1$-$C_8$-alkylsulphinyl, $C_1$-$C_8$-halogenoalkylsulphinyl comprising up to 9 halogen atoms which can be the same or different, $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkoxyimino)-$C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-; benzyloxy which can be substituted by up to 5 groups Q; benzylsulfanyl which can be substituted by up to 5 groups Q; benzylamino which can be substituted by up to 5 groups Q; naphtyl which can be substituted by up to 6 groups Q; phenoxy which can be substituted by up to 5 groups Q; phenylamino which can be substituted by up to 5 groups Q; phenylsulfanyl which can be substituted by up to 5 groups Q; phenylmethylene which can be substituted by up to 5 groups Q; pyridinyl which can be substituted by up to four groups Q and pyridinyloxy which can be substituted by up to four groups Q;
  two substituents X together with the consecutive carbon atoms to which they are linked can form a 5- or 6-membered, saturated, carbo- or hetero-cycle, which can be substituted by up to four groups Q which can be the same or different;

n represents 1, 2, 3, 4 or 5;

R, which can be the same or different, represent hydrogen atom; halogen atom; cyano; nitro; amino; sulfanyl; pentafluoro-λ-6-sulfanyl; $C_1$-$C_8$-alkylamino; tri($C_1$-$C_8$-alkyl)silyl; $C_1$-$C_8$-alkylsulfanyl; $C_1$-$C_8$-halogenoalkylsulfanyl comprising up to 9 halogen atoms which can be the same or different; $C_1$-$C_8$-halogenoalkyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different; $C_1$-$C_8$-alkoxy; $C_1$-$C_8$-halogenoalkoxy comprising up to 9 halogen atoms which can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$-alkylsulphinyl; $C_1$-$C_8$-alkylsulphonyl; $C_1$-$C_8$alkoxyimino; ($C_1$-$C_8$-alkoxyimino)-$C_1$-$C_8$-alkyl; (benzyloxyimino)-$C_1$-$C_8$-alkyl; phenoxy; benzyloxy; benzylsulfanyl; benzylamino; naphtyl; halogenophenoxy comprising up to 9 halogen atoms which can be the same or different; $C_1$-$C_8$-alkylcarbonyl; $C_1$-$C_8$-halogenoalkylcarbonyl comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl;

Q, which can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$)alkylsilyl and tri($C_1$-$C_8$)alkylsilyl-$C_1$-$C_8$-alkyl;

as well as salts, N-oxides, metallic complexes, metalloidic complexes and optically active or geometric isomers thereof; with the exception of 2-furancarboxamide, N-(1,3-benzodioxol-5-ylmethyl)-N-cyclopentyl-5-methyl and 2-furancarboxamide, N-(1,3-benzodioxol-5-ylmethyl)-N-cyclopentyl-2,5-dimethyl.

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulfur.

Preferred compounds according to the invention are compounds of formula (I) wherein A is selected in the list consisting of:

a heterocycle of formula ($A^1$)

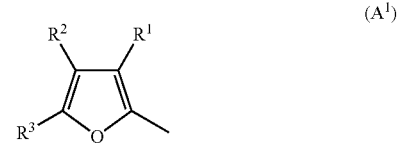

wherein:
$R^1$ to $R^3$ which can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;

a heterocycle of formula ($A^2$)

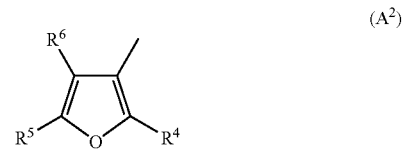

wherein:
$R^4$ to $R^6$ which can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;

a heterocycle of formula ($A^3$)

wherein:
$R^7$ represents a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;
$R^8$ represents a hydrogen atom or a $C_1$-$C_5$-alkyl;

a heterocycle of formula ($A^4$)

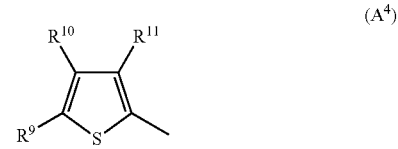

wherein:
R$^9$ to R$^{11}$ which can be the same or different represent a hydrogen atom; a halogen atom; C$_1$-C$_5$-alkyl; amino; C$_1$-C$_5$-alkoxy; C$_1$-C$_5$-alkylthio C$_1$-C$_5$-halogenoalkyl comprising up to 9 halogen atoms which can be the same or different or C$_1$-C$_5$-halogenoalkoxy comprising up to 9 halogen atoms which can be the same or different;
a heterocycle of formula (A$^5$)

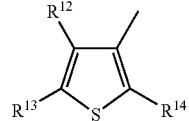

wherein:
R$^{12}$ and R$^{13}$ which can be the same or different represent a hydrogen atom; a halogen atom; C$_1$-C$_5$-alkyl; C$_1$-C$_5$-alkoxy; amino; C$_1$-C$_5$-halogenoalkyl comprising up to 9 halogen at which can be the same or different or C$_1$-C$_5$-halogenoalkoxy comprising up to 9 halogen atoms which can be the same or different;
R$^{14}$ represents a hydrogen atom; a halogen atom; C$_1$-C$_5$-alkyl; C$_1$-C$_5$-alkoxy; amino; C$_1$-C$_5$-halogenoalkyl comprising up to 9 halogen atoms which can be the same or different or C$_1$-C$_5$-halogenoalkoxy comprising up to 9 halogen atoms which can be the same or different;
a heterocycle of formula (A$^6$)

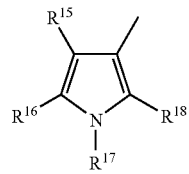

wherein:
R$^{15}$ represents a hydrogen atom; a halogen atom; a cyano; C$_1$-C$_5$-alkyl; C$_1$-C$_5$-alkoxy; C$_1$-C$_5$-halogenoalkoxy comprising up to 9 halogen atoms which can be the same or different or C$_1$-C$_5$-halogenoalkyl comprising up to 9 halogen atoms which can be the same or different;
R$^{16}$ and R$^{18}$ which can be the same or different represent a hydrogen atom; a halogen atom; C$_1$-C$_5$-alkoxycarbonyl; C$_1$-C$_5$-alkyl; C$_1$-C$_5$-halogenoalkoxy comprising up to 9 halogen atoms which can be the same or different or C$_1$-C$_5$-halogenoalkyl comprising up to 9 halogen atoms which can be the same or different;
R$^{17}$ represent a hydrogen atom or C$_1$-C$_5$-alkyl;
a heterocycle of formula (A$^7$)

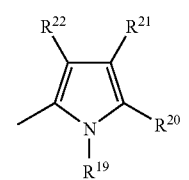

wherein:
R$^{19}$ represents a hydrogen atom or a C$_1$-C$_5$-alkyl
R$^{20}$ to R$^{22}$ which can be the same or different represent a hydrogen atom; a halogen atom; C$_1$-C$_5$-alkyl or C$_1$-C$_5$-halogenoalkyl comprising up to 9 halogen atoms which can be the same or different;
a heterocycle of formula (A$^8$)

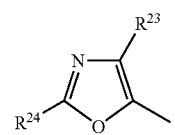

wherein:
R$^{23}$ represents a hydrogen atom; a halogen atom; C$_1$-C$_5$-alkyl or C$_1$-C$_5$-halogenoalkyl comprising up to 9 halogen atoms which can be the same or different;
R$^{24}$ represents a hydrogen atom or C$_1$-C$_5$-alkyl or C$_1$-C$_5$-halogenoalkyl comprising up to 9 halogen atoms which can be the same or different;
a heterocycle of formula (A$^9$)

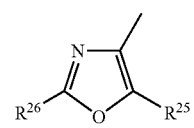

wherein:
R$^{25}$ represents a hydrogen atom; a halogen atom; C$_1$-C$_5$-alkyl or C$_1$-C$_5$-halogenoalkyl comprising up to 9 halogen atoms which can be the same or different;
R$^{26}$ represents a hydrogen atom; C$_1$-C$_5$-alkyl or C$_1$-C$_5$-halogenoalkyl comprising up to 9 halogen atoms which can be the same or different;
a heterocycle of formula (A$^{10}$)

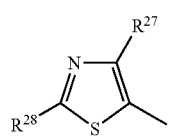

wherein:
R$^{27}$ represents a hydrogen atom; a halogen atom; C$_1$-C$_5$-alkyl or C$_1$-C$_5$-halogenoalkyl comprising up to 9 halogen atoms which can be the same or different;
R$^{28}$ represents a hydrogen atom; a halogen atom; amino; C$_1$-C$_5$-alkyl or C$_1$-C$_5$-halogenoalkyl comprising up to 9 halogen atoms which can be the same or different;
a heterocycle of formula (A$^{11}$)

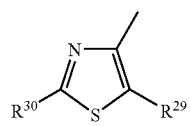

wherein:

$R^{29}$ represents a hydrogen atom; a halogen atom; $C_1$-$C_5$-alkyl; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;

$R^{30}$ represents a hydrogen atom; a bromine atom; a fluorine atom; an iodine atom; $C_1$-$C_5$-alkyl; $C_1$-$C_5$-halogenoalkyl comprising up to 9 halogen atoms which can be the same or different; $C_1$-$C_5$-halogenoalkoxy comprising up to 9 halogen atoms which can be the same or different; amino; $C_1$-$C_5$-alkylamino or di-$C_1$-$C_5$-alkylamino;

a heterocycle of formula ($A^{12}$)

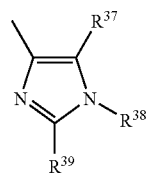

wherein:

$R^{31}$ represents a hydrogen atom; a halogen atom or a $C_1$-$C_5$-alkyl $R^{32}$ represents a hydrogen atom; a halogen atom; $C_1$-$C_5$-alkyl or $C_1$-$C_5$-halogenoalkyl comprising up to 9 halogen atoms which can be the same or different;

$R^{33}$ represents a hydrogen atom; a halogen atom; a nitro; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;

a heterocycle of formula ($A^{13}$)

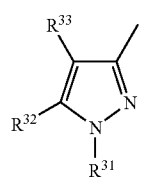

wherein:

$R^{34}$ represents a hydrogen atom; a halogen atom; $C_1$-$C_5$-alkyl; $C_3$-$C_5$-cycloalkyl; $C_1$-$C_5$-halogenoalkyl comprising up to 9 halogen atoms which can be the same or different; $C_1$-$C_5$-alkoxy; $C_2$-$C_5$-alkynyloxy or $C_1$-$C_5$-halogenoalkoxy comprising up to 9 halogen atoms which can be the same or different;

$R^{35}$ represents a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 9 halogen atoms which can be the same or different; $C_1$-$C_5$-halogenoalkoxy comprising up to 9 halogen atoms which can be the same or different; amino; $C_1$-$C_5$-alkylamino or di($C_1$-$C_5$-alkyl)amino;

$R^{36}$ represents a hydrogen atom or $C_1$-$C_5$-alkyl;

a heterocycle of formula ($A^{14}$)

($A^{14}$)

wherein:

$R^{37}$ and $R^{39}$ which can be the same or different represent a hydrogen atom; a halogen atom; $C_1$-$C_5$-alkyl or $C_1$-$C_5$-halogenoalkyl comprising up to 9 halogen atoms which can be the same or different;

$R^{38}$ represents a hydrogen atom or $C_1$-$C_5$-alkyl;

a heterocycle of formula ($A^{15}$)

($A^{15}$)

wherein:

$R^{40}$ and $R^{41}$ which can be the same or different represent a hydrogen atom; a halogen atom; $C_1$-$C_5$-alkyl or $C_1$-$C_5$-halogenoalkyl comprising up to 9 halogen atoms which can be the same or different;

a heterocycle of formula ($A^{16}$)

($A^{16}$)

wherein:

$R^{42}$ and $R^{43}$ which can be the same or different represent a hydrogen atom; a halogen atom; $C_1$-$C_5$-alkyl; $C_1$-$C_5$-halogenoalkyl comprising up to 9 halogen atoms which can be the same or different or amino;

a heterocycle of formula ($A^{17}$)

($A^{17}$)

wherein:

$R^{44}$ and $R^{45}$ which can be the same or different represent a hydrogen atom; a halogen atom; $C_1$-$C_5$-alkyl or $C_1$-$C_5$-halogenoalkyl comprising up to 9 halogen atoms which can be the same or different;

$R^{46}$ represents a hydrogen atom or $C_1$-$C_5$-alkyl;

a heterocycle of formula (A¹⁸)

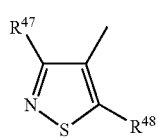

wherein:
R⁴⁷ represents a hydrogen atom; a halogen atom; $C_1$-$C_5$-alkyl or $C_1$-$C_5$-halogenoalkyl comprising up to 9 halogen atoms which can be the same or different;
R⁴⁸ represents a hydrogen atom; a halogen atom; $C_1$-$C_5$-alkyl; $C_1$-$C_5$-halogenoalkyl comprising up to 9 halogen atoms which can be the same or different or $C_1$-$C_5$-alkylsulfanyl;
a heterocycle of formula (A¹⁹)

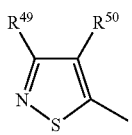

wherein:
R⁴⁹ and R⁵⁰ which can be the same or different represent a hydrogen atom; a halogen atom; $C_1$-$C_5$-alkyl; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;
a heterocycle of formula (A²⁰)

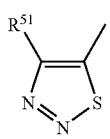

wherein:
R⁵¹ represents a hydrogen atom; a halogen atom; $C_1$-$C_5$-alkyl or $C_1$-$C_5$-halogenoalkyl comprising up to 9 halogen atoms which can be the same or different;
a heterocycle of formula (A²¹)

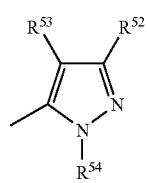

wherein:
R⁵² and R⁵³ which can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or a $C_1$-$C_5$-alkylthio;
R⁵⁴ represents a hydrogen atom or $C_1$-$C_5$-alkyl;

a heterocycle of formula (A²²)

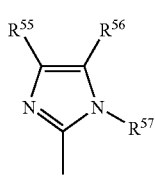

wherein:
R⁵⁵ and R⁵⁶ which can be the same or different represent a hydrogen atom; a halogen atom; $C_1$-$C_5$-alkyl or $C_1$-$C_5$-halogenoalkyl comprising up to 9 halogen atoms which can be the same or different;
R⁵⁷ represents a hydrogen atom or $C_1$-$C_5$-alkyl.

More preferred compounds according to the invention are compounds of formula (I) wherein A is selected in the list consisting of $A^2$; $A^6$; $A^{10}$ and $A^{13}$ as herein-defined.

Other preferred compounds according to the invention are compounds of formula (I) wherein $Z^1$ represents a non substituted $C_3$-$C_7$-cycloalkyl; more preferably $Z^1$ represents cyclopropyl.

Other preferred compounds according to the invention are compounds of formula (I) wherein $Z^1$ represents a $C_3$-$C_7$ cycloalkyl substituted by up to 10 groups or atoms which can be the same or different and which can be selected ion in the list consisting of halogen atoms; $C_1$-$C_8$-alkyl; $C_1$-$C_8$-halogenoalkyl comprising up to 9 halogen atoms which can be the same or different; $C_1$-$C_8$-alkoxy or $C_1$-$C_8$-halogenoalkoxy comprising up to 9 halogen atoms which can be the same or different.

Other preferred compounds according to the invention are compounds of formula (I) wherein X, which can be the same or different, represents a halogen atom; $C_1$-$C_8$-alkyl; $C_1$-$C_8$-halogenoalkyl comprising up to 9 halogen atoms which can be the same or different; $C_1$-$C_8$-alkoxy or $C_1$-$C_8$-halogenoalkoxy comprising up to 9 halogen atoms which can be the same or different.

More preferred compounds according to the invention are compounds of formula (I) wherein two consecutive substituents X together with the phenyl ring form a substituted or non substituted 1,3-benzodioxolyl; 1,2,3,4-tetrahydro-quinoxalinyl; 3,4-dihydro-2H-1,4-benzoxazinyl; 1,4-benzodioxanyl; indanyl; 2,3-dihydrobenzofuranyl; indolinyl.

Other preferred compounds according to the invention are compounds of formula (I) wherein R, which can be the same or different, represents a hydrogen atom; halogen atom; cyano; $C_1$-$C_8$-alkylamino; di-$C_1$-$C_8$-alkylamino; tri($C_1$-$C_8$-alkyl)silyl; $C_1$-$C_8$-alkyl; $C_1$-$C_8$-halogenoalkyl comprising up to 9 halogen atoms which can be the same or different; $C_1$-$C_8$-alkoxy; $C_1$-$C_8$-halogenoalkoxy comprising up to 9 halogen atoms which can be the same or different; $C_1$-$C_8$-alkylsulfanyl; amino, hydroxyl; nitro; $C_1$-$C_8$-alkoxycarbonyl; $C_2$-$C_8$-alkynyloxy.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combined:
preferred features of A with preferred features of $Z^1$;
preferred features of A with preferred features of $Z^2$ or $Z^3$;
preferred features of A with preferred features of X and n;

preferred features of A with preferred features of R or Q;
preferred features of A with preferred features of $Z^1$ and $Z^2$ or $Z^3$;
preferred features of A with preferred features of $Z^1$ and X and n;
preferred features of A with preferred features $Z^1$ and R or Q;
preferred features of $Z^1$ with preferred features of $Z^2$ or $Z^3$;
preferred features of $Z^1$ with preferred features of X and n;
preferred features of $Z^1$ with preferred features of R or Q;
preferred features of $Z^2$ or $Z^3$ with preferred features of X and n;
preferred features of $Z^2$ or $Z^3$ with preferred features of R or Q.

In these combinations of preferred features of the substituents of the compounds according to the invention, the said preferred features can also be selected among the more preferred features of each of A, $Z^1$, $Z^3$, $Z^3$, X, n, R and Q so as to form most preferred subclasses of compounds according to the invention.

The present invention also relates to a process for the preparation of compounds of formula (I). Thus according to a further aspect of the present invention there is provided a process P1 for the preparation of compound of formula (I) as herein-defined, as illustrated by the following reaction scheme:

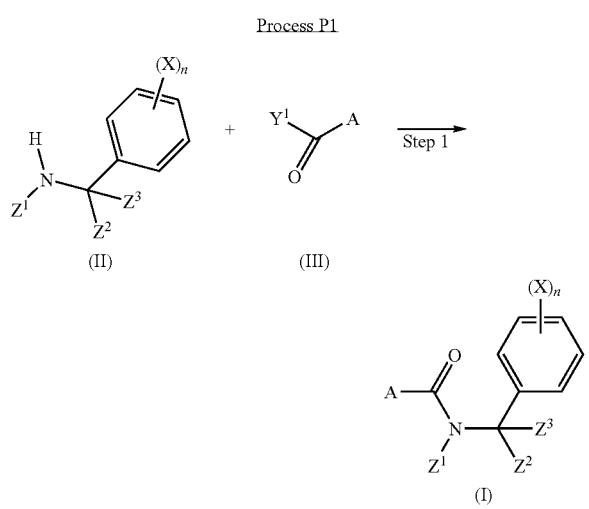

wherein
A, $Z^1$, $Z^2$, $Z^3$, X and n are as herein-defined;
$Y^1$ represents a halogen or a hydroxyl.

According to a further aspect of the present invention there is provided a process P2 for the preparation of compound of formula (I) as herein-defined, as illustrated by the following reaction scheme:

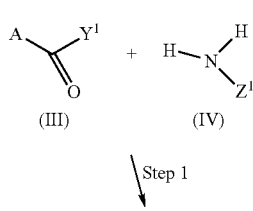

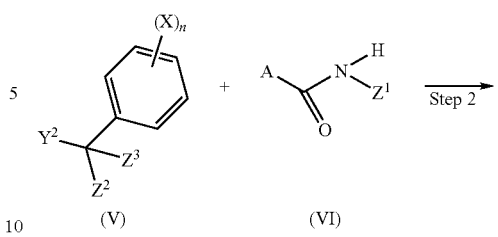

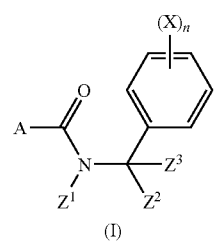

wherein
A, $Z^1$, $Z^2$, $Z^3$, X and n are as herein-defined;
$Y^1$ represents a halogen or a hydroxyl;
$Y^2$ represents a halogen or a leaving group like a tosylate group.

In processes P1 and P2 according to the invention, step 1 may be performed if appropriate in the presence of a solvent and if appropriate in the presence of an acid binder.

In processes P2 according to the invention, step 2 may be performed if appropriate in the presence of a solvent and if appropriate in the presence of an acid binder.

N-cycloalkyl-amine derivatives of formula (II) are known or can be prepared by known processes (J. Het. Chem., 1983, p 1031-6; J. Am. Chem. Soc., 2004, p 5192-5201; Synt. Comm. 2003, p 3419-25).

Carboxylic acid derivatives of formula (III) are known or can be prepared by known processes (WO-93/11117; EP-A 0 545 099; Nucleosides & Nucleotides, 1987, p 737-759, Bioorg. Med. Chem., 2002, p 2105-2108).

Benzyl derivatives of formula (V) and cycloalkylamine derivatives of formula (IV) are known.

When X represents a halogen atom, processes P1 and P2 according to the invention for the preparation of compound of formula (I) may optionally be completed by a further step.

Process P3 according to the invention of such a step can be illustrated by the following reaction scheme:

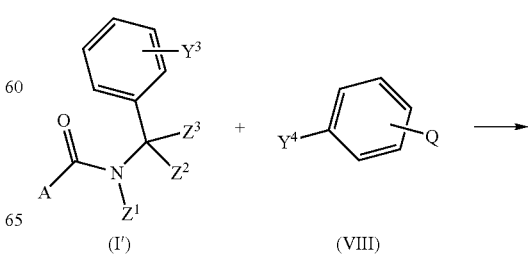

-continued

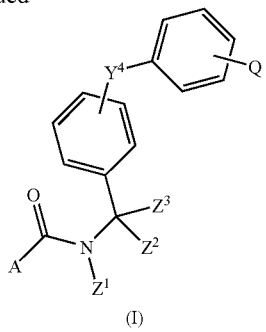

(I)

wherein
A, $Z^1$, $Z^2$, $Z^3$, X, Q and n are as herein-defined;
$Y^3$ represents a halogen atom;
$Y^4$ represents sulphur, oxygen or $C_1$-$C_5$-alkylamino.

Process P3 according to the invention may be performed in the presence of a acid binder and if appropriate in the presence of a solvent;

Phenol, thiophenol or aniline derivatives of formula (VIII) are known.

Suitable acid binder for carrying out processes P1, P2 and P3 according to the invention are in each case all inorganic and organic bases which are customary for such reactions. Preference is given to using alkaline earth metal, alkali metal hydride, alkali metal hydroxides or alkali metal alkoxydes, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also ternary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

It is also possible to work in the absence of an additional condensing agent or to employ an excess of the amine component, so that it simultaneously acts as acid binder agent.

Suitable solvents for carrying out processes P1, P2 and P3 according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Process P3 according to the invention is preferably carried out in the presence of a catalyst, such as a metal salt or complex. Suitable metal for this purpose are preferably copper or palladium. Suitable salts or complexes for this purpose are copper chloride, copper iodide, copper oxide, palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition of a palladium salt and a complex ligand, such as triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenyl)-phosphine, 2,2'-bis(diphenylphosphine)-1,1'-binaphthyl, 1,4-bis(diphenylphosphine)butane, 1,2-bis(diphenylphosphine)ethane, 1,4-bis(dicyclohexylphosphine)butane, 1,2-bis(dicyclo-hexylphosphine)ethane, 2-(dicyclohexylphosphine)-2'-(N,N-dimethylamino)-biphenyl, bis(diphenylphosphino)ferrocene or tris-(2,4-tert-butylphenyl)phosphite to the reaction.

When carrying out processes P1, P2 and P3 according to the invention, the reaction temperatures can independently be varied within a relatively wide range. Generally, processes according to the invention are carried out at temperatures between 0° C. and 160° C., preferably between 10° C. and 120° C.

Processes P1, P2 and P3 according to the invention are generally independently carried out under atmospheric pressure. However, in each case, it is also possible to operate under elevated or reduced pressure.

When carrying out step 1 of processes P1 or P2 according to the invention, generally 1 mol or other an excess of the acid derivative of formula (III) and from 1 to 3 mol of acid binder are employed per mole of amine of formula (II) or (IV). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

When carrying out step 2 of process P2 according to the invention, generally 1 mol or other an excess of benzyl derivative of formula (V) and from 1 to 3 mol of acid binder are employed per mole of amide of formula (VI). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can, be freed by customary methods, such as chromatography or recrystallization, from any impurities that may still be present.

When carrying out process P3 according to the invention, generally 1 mol or other of an excess of the phenol, thiophenol or aniline derivative of formula (VIII) and from 1 to 10 mol of acid binder and from 0.5 to 5 mol percent of a catalyst are employed per mole of amide derivative of formula (I'). It is also possible to employ the reaction components in other ratios.

Work-up is carried out by customary methods. Generally, the reaction mixture is concentrated under reduced pressure. If appropriate, the remaining residue can, be freed by customary methods, such as chromatography or recrystallization, from any impurities that may still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilizers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilizers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous.

Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example
as CI-respiration inhibitor like diflumetorim;
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, pyribencarb, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B11) a compound capable to inhibit melanine biosynthesis like carprop

B10) a compound capable to inhibit cell wall synthesis like benthiavalicarb, bialaphos, dimethomorph, flumorph, iprovalicarb, polyoxins, polyoxorim, validamycin A; amid, diclocymet, fenoxanil, phtalide, pyroquilon, tricyclazole;

B12) a compound capable to induce a host defense like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, valiphenal, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxy-benzamide, 2-[[[[1-[3(1-Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, N-{2-[1,1'-bi(cyclopropyl)-2-yl]phenyl}-3-(difluoromethyl)-1-methyl-1H-pyrazole-4-carboxamide, N'-{5-(difluoromethyl)-2-methyl-4-[3-(trimethylsilyl)propoxy]phenyl}-N-ethyl-N-methylimidoformamide, N'-{5-(trifluoromethyl)-2-methyl-4-[3-(trimethylsilyl)propoxy]phenyl}-N-ethyl-N-methylimidoformamide.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterized in that a compound of formula (I) or a fungicide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the invention, mention may be made of:

Powdery mildew diseases such as:
- Blumeria diseases, caused for example by *Blumeria graminis*;
- Podosphaera diseases, caused for example by *Podosphaera leucotricha*;
- Sphaerotheca diseases, caused for example by *Sphaerotheca fuliginea*;
- Uncinula diseases, caused for example by *Uncinula necator*;

Rust diseases such as:
- Gymnosporangium diseases, caused for example by *Gymnosporangium sabinae*;
- Hemileia diseases, caused for example by *Hemileia vastatrix*;
- Phakopsora diseases, caused for example by *Phakopsora pachyrhizi* or *Phakopsora meibomiae*;
- Puccinia diseases, caused for example by *Puccinia recondita*;
- Uromyces diseases, caused for example by *Uromyces appendiculatus*;

Oomycete diseases such as:
- Bremia diseases, caused for example by *Bremia lactucae*;
- Peronospora diseases, caused for example by *Peronospora pisi* or *P. brassicae*;
- Phytophthora diseases, caused for example by *Phytophthora infestans*;
- Plasmopara diseases, caused for example by *Plasmopara viticola*;
- Pseudoperonospora diseases, caused for example by *Pseudoperonospora humuli* or *Pseudoperonospora cubensis*;
- Pythium diseases, caused for example by *Pythium ultimum*;

Leafspot, leaf blotch and leaf blight diseases such as:
- Alternaria diseases, caused for example by *Alternia solani*;
- Cercospora diseases, caused for example by *Cercospora beticola*;
- Cladiosporum diseases, caused for example by *Cladiosporium cucumetinum*;
- Cochliobolus diseases, caused for example by *Cochliobolus sativus*;
- Colletotrichum diseases, caused for example by *Colletotrichum lindemuthanium*;
- Cycloconium diseases, caused for example by *Cycloconium oleaginum*;
- Diaporthe diseases, caused for example by *Diaporthe citri*;
- Elsinoe diseases, caused for example by *Elsinoe fawcettii*;
- Gloeosporium diseases, caused for example by *Gloeosporium laeticolor*;
- Glomerella diseases, caused for example by *Glomerella cingulata*;
- Guignardia diseases, caused for example by *Guignardia bidwelli*;
- Leptosphaeria diseases, caused for example by *Leptosphaeria maculans*; *Leptosphaeria nodorum*;
- Magnaporthe diseases, caused for example by *Magnaporthe grisea*;
- Mycosphaerella diseases, caused for example by *Mycosphaerella graminicola*; *Mycosphaerella arachidicola*; *Mycosphaerella fijiensis*;
- Phaeosphaeria diseases, caused for example by *Phaeosphaeria nodorum*;
- Pyrenophora diseases, caused for example by *Pyrenophora teres*;
- Ramularia diseases, caused for example by *Ramularia collo-cygni*;
- Rhynchosporium diseases, caused for example by *Rhynchosporium secalis*;
- Septoria diseases, caused for example by *Septoria apii* or *Septoria lycopercisi*;
- Typhula diseases, caused for example by *Typhula incamata*;
- Venturia diseases, caused for example by *Venturia inaequalis*;

Root and stem diseases such as:
- Corticium diseases, caused for example by *Corticium graminearum*;
- Fusarium diseases, caused for example by *Fusarium oxysporum*;
- Gaeumannomyces diseases, caused for example by *Gaeumannomyces graminis*;
- Rhizoctonia diseases, caused for example by *Rhizoctonia solani*;
- Tapesia diseases, caused for example by *Tapesia acuformis*;
- Thielaviopsis diseases, caused for example by *Thielaviopsis basicola*;

Ear and panicle diseases such as:
- Alternaria diseases, caused for example by *Alternia* spp.;
- Aspergillus diseases, caused for example by *Aspergillus flavus*;
- Cladosporium diseases, caused for example by *Cladosporium* spp.;
- Claviceps diseases, caused for example by *Claviceps purpurea*;
- Fusarium diseases, caused for example by *Fusarium culmorum*;
- Gibberella diseases, caused for example by *Gibberella zeae*;
- Monographella diseases, caused for example by *Monographella nivalis*;

Smut and bunt diseases such as:
- Sphacelotheca diseases, caused for example by *Sphacelotheca reiliana*;
- Tilletia diseases, caused for example by *Tilletia caries*;
- Urocystis diseases, caused for example by *Urocystis occulta*;
- Ustilago diseases, caused for example by *Ustilago nuda*;

Fruit rot and mould diseases such as:
- Aspergillus diseases, caused for example by *Aspergillus flavus*;
- Botrytis diseases, caused for example by *Botrytis cinerea*;
- Penicillium diseases, caused for example by *Penicillium expansum*;
- Sclerotinia diseases, caused for example by *Sclerotinia sclerotiorum*;
- Verticilium diseases, caused for example by *Verticilium alboatrum*;

Seed and soilborne decay, mould, wilt, rot and damping-off diseases:
    Fusarium diseases, caused for example by *Fusarium culmorum*;
    Phytophthora diseases, caused for example by *Phytophthora cactorum*;
    Pythium diseases, caused for example by *Pythium ultimum*;
    Rhizoctonia diseases, caused for example by *Rhizoctonia solani*;
    Sclerotium diseases, caused for example by *Sclerotium rolfsii*;
    Microdochium diseases, caused for example by *Microdochium nivale*;
Canker, broom and dieback diseases such as:
    Nectria diseases, caused for example by *Nectria galligena*;
Blight diseases such as:
    Monilinia diseases, caused for example by *Monilinia laxa*;
Leaf blister or leaf curl diseases such as:
    Taphrina diseases, caused for example by *Taphrina deformans*;
Decline diseases of wooden plants such as:
    Esca diseases, caused for example by *Phaemoniella clamydospora*;
    Eutypa dyeback, caused for example by *Eutypa lata*;
    Dutch elm disease, caused for example by *Ceratocystsc ulmi*;
Diseases of flowers and Seeds such as:
    Botrytis diseases, caused for example by *Botrytis cinerea*;
Diseases of tubers such as:
    Rhizoctonia diseases, caused for example by *Rhizoctonia solani*.

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is dearly understood that the doses indicated herein are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following tables of compound examples and the following preparation or efficacy examples.

The following tables illustrate in a non-limiting manner examples of compounds according to the invention. The compound example tables display compounds according to the invention of specific formulae (I-A$^1$) to (I-A$^{22}$).

In the following compound examples, M+H (or M–H) means the molecular ion peak, plus or minus 1 a.m.u. (atomic mass unit) respectively, as observed in mass spectroscopy and M (Apcl+) means the molecular ion peak as it was found via positive atmospheric pressure chemical ionization in mass spectroscopy.

In the following examples, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones).

The lambda max values were determined in the maxima of the chromatographic signals using the UV spectra from 190 nm to 400 nm.

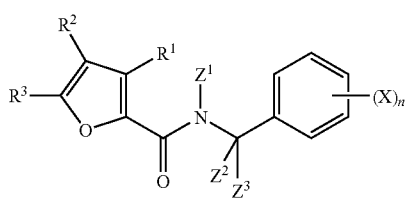

I-A$^1$

| N° | R$^1$ | R$^2$ | R$^3$ | Z$^2$ | Z$^3$ | Z$^1$ | (X)$_n$ | LogP | M+H |
|---|---|---|---|---|---|---|---|---|---|
| 1 | Me | H | H | H | H | Cyclopropyl | 2-Cl-4-Cl | | 324 |
| 2 | Me | H | H | H | H | Cyclopropyl | 2-Cl-4-CF3 | | |
| 3 | H | H | H | H | H | Cyclopropyl | 2-Cl-4-Cl | | 310 |
| 4 | H | H | H | H | H | Cyclopropyl | 2-Cl-4-CF3 | | |
| 5 | Me | H | H | H | H | Cyclopropyl | 2-Cl-4-Cl-6-Cl | | 358 |
| 6 | H | H | H | H | H | Cyclopropyl | 2-Cl-4-Cl-6-Cl | | 344 |

-continued

I-A¹

| N° | R¹ | R² | R³ | Z² | Z³ | Z¹ | (X)ₙ | LogP | M+H |
|----|----|----|----|----|----|----|------|------|-----|
| 7 | Me | H | H | H | H | 3,5,5-trimethyl-cyclohexyl | 2-Cl-4-Cl-6-Cl | | |
| 8 | Me | H | H | H | H | cycloheptyl | 2-Cl-4-Cl-6-Cl | | |

I-A²

| N° | R⁴ | R⁶ | R⁵ | Z² | Z³ | Z¹ | (X)ₙ | LogP | M+H |
|----|----|----|----|----|----|----|------|------|-----|
| 9 | Me | H | H | H | H | Cyclopropyl | 2-Cl-4-CF3 | | |
| 10 | CF3 | Me | H | H | H | Cyclopropyl | 2-Cl-4-CF3 | | |
| 11 | Me | H | H | H | H | Cyclopropyl | 2-Cl-4-Cl | 3.77 | |
| 12 | CF3 | Me | H | H | H | Cyclopropyl | 2-Cl-4-Cl | 4.6 | |
| 13 | Me | H | H | H | H | Cyclopropyl | 2-Cl-4-Cl-6-Cl | 4.09 | |
| 14 | CF3 | Me | H | H | H | Cyclopropyl | 2-Cl-4-Cl-6-Cl | 4.91 | |
| 15 | Me | H | H | H | H | Cyclopropyl | 4-CF3 | 3.43 | |
| 16 | CF3 | Me | H | H | H | Cyclopropyl | 4-CF3 | 4.18 | |
| 17 | Me | H | H | Me | H | Cyclopropyl | 4-CF3 | | 338 |
| 18 | CF3 | Me | H | Me | H | Cyclopropyl | 4-CF3 | | 406 |
| 19 | Me | H | H | H | H | Cyclopropyl | 4-OPh | | 348 |
| 20 | CF3 | Me | H | H | H | Cyclopropyl | 4-OPh | | 416 |
| 21 | Me | H | H | H | H | Cyclopropyl | 4-O(2-Cl-4-Cl—Ph) | | 416 |
| 22 | I | H | H | H | H | Cyclopropyl | 2-Cl-4-Cl | | |
| 23 | I | H | H | H | H | Cyclopropyl | 2-Cl-4-CF3 | | |
| 24 | Me | Me | H | H | H | Cyclopropyl | 2-Cl-4-Cl | | 338 |
| 25 | Me | Me | H | H | H | Cyclopropyl | 2-Cl-4-CF3 | | 372 |
| 26 | I | H | H | H | H | Cyclopropyl | 2-Cl-4-Cl-6-Cl | | |
| 27 | Me | Me | H | H | H | Cyclopropyl | 2-Cl-4-Cl-6-Cl | | 372 |
| 28 | Me | Me | H | H | H | Cyclopropyl | 2-OMe-5-Ac | | 342 |
| 29 | Me | Me | H | H | H | Cyclopropyl | 3-Cl-5-Cl | | 338 |
| 30 | Me | Me | H | H | H | Cyclopropyl | 3-Me | | 284 |
| 31 | Me | Me | H | H | H | Cyclopropyl | 3-Me-4-Me | | |
| 32 | Me | Me | H | H | H | Cyclopropyl | 4-i-Pr | | 312 |
| 33 | Me | Me | H | H | H | Cyclopropyl | 2-CN | | |
| 34 | Me | Me | H | H | H | Cyclopropyl | 4-CN | | 295 |
| 35 | Me | Me | H | H | H | Cyclopropyl | 2-OMe | | 299 |
| 36 | Me | Me | H | H | H | Cyclopropyl | 2-Me-4-Me-6-Me | | |
| 37 | Me | Me | H | H | H | Cyclopropyl | 3,4-Methylenedioxy | | |
| 38 | Me | Me | H | H | H | Cyclopropyl | 2-OMe-5-OMe | | |
| 39 | Me | Me | H | H | H | Cyclopropyl | 3-OCF3 | | 354 |
| 40 | Me | Me | H | H | H | Cyclopropyl | 2-Cl-4, 5-Methylenedioxy | | 348 |
| 41 | Me | Me | H | Me | H | Cyclopropyl | 2-Cl-4-Cl | | 352 |
| 42 | Me | Me | H | Et | H | Cyclopropyl | 2-Cl-4-Cl | | 366 |
| 43 | Me | Me | H | H | H | 3,5,5-trimethyl-cyclohexyl | 2-Cl-4-Cl-6-Cl | | |
| 44 | Me | Me | H | H | H | cycloheptyl | 2-Cl-4-Cl-6-Cl | | |
| 45 | I | H | H | H | H | 3,5,5-trimethyl-cyclohexyl | 2-Cl-4-Cl-6-Cl | | |

-continued

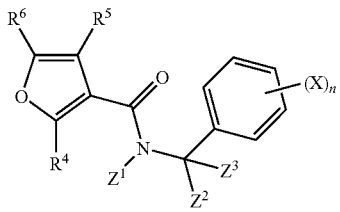

I-A²

| N° | R⁴ | R⁶ | R⁵ | Z² | Z³ | Z¹ | (X)ₙ | LogP | M + H |
|----|----|----|----|----|----|-----|------|------|-------|
| 46 | I  | H  | H  | H  | H  | cycloheptyl | 2-Cl-4-Cl-6-Cl | | |
| 47 | Me | Me | H  | n-Pr | H | Cyclopropyl | 2-Cl-4-Cl | | 380 |
| 48 | Me | Me | H  | Me | H  | Cyclopropyl | 2-Cl-5-CF3 | | 386 |
| 49 | Me | Me | H  | H  | H  | Cyclopropyl | 2-Cl-5-CF3 | | 372 |
| 50 | Me | Me | H  | H  | H  | Cyclopropyl | 2-CF3-5-Cl | | 372 |
| 51 | Me | Me | H  | Me | H  | Cyclopropyl | 4-CF3 | | 352 |
| 52 | I  | H  | H  | H  | H  | Cyclopentyl | 2-Cl-4-Cl-6-Cl | | |

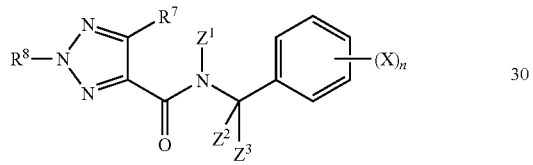

I-A³

| N° | R⁷ | R⁸ | Z² | Z³ | Z¹ | (X)ₙ | LogP | M + H |
|----|----|----|----|----|-----|------|------|-------|
| 53 | CF3 | Me | H | H | Cyclopropyl | 2-Cl-4-CF3 | | |
| 54 | CF3 | Me | H | H | Cyclopropyl | 2-Cl-4-Cl | | 393 |
| 55 | CF3 | Me | H | H | Cyclopropyl | 2-Cl-4-Cl-6-Cl | | |
| 56 | CF3 | Me | H | H | Cyclopropyl | 3-OPh-4-F | | 435 |

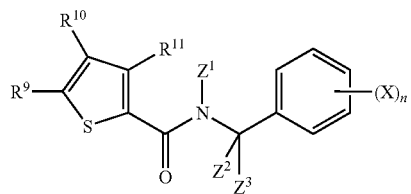

I-A⁴

| N° | R⁹ | R¹⁰ | R¹¹ | Z² | Z³ | Z¹ | (X)ₙ | LogP | M + H |
|----|----|-----|-----|----|----|-----|------|------|-------|
| 57 | H | H | I | H | H | Cyclopropyl | 2-Cl-4-CF3 | | |
| 58 | H | H | I | H | H | Cyclopropyl | 2-Cl-4-Cl | 4.48 | |
| 59 | H | H | I | H | H | Cyclopropyl | 2-Cl-4-Cl-6-Cl | 4.86 | |
| 60 | H | H | I | H | H | Cyclopropyl | 4-CF3 | 4.04 | |
| 61 | H | H | I | Me | H | Cyclopropyl | 4-CF3 | | 466 |
| 62 | H | H | I | H | H | Cyclopropyl | 4-OPh | | 476 |
| 63 | H | H | I | H | H | 3,5,5-trimethyl-cyclohexyl | 2-Cl-4-Cl-6-Cl | | |
| 64 | H | H | I | H | H | cycloheptyl | 2-Cl-4-Cl-6-Cl | | |

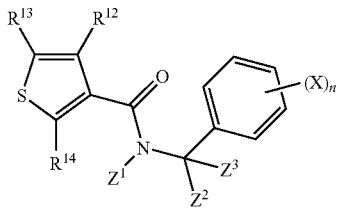

I-A⁵

| N° | R¹² | R¹³ | R¹⁴ | Z² | Z³ | Z¹ | (X)ₙ | LogP | M + H |
|---|---|---|---|---|---|---|---|---|---|
| 65 | H | H | I | H | H | Cyclopropyl | 2-Cl-6-Cl | | 452 |
| 66 | OMe | H | H | H | H | Cyclopropyl | 2-Cl-4-Cl | | |
| 67 | OMe | H | H | H | H | Cyclopropyl | 2-Cl-4-CF3 | | |
| 68 | OMe | H | H | H | H | Cyclopropyl | 2-Cl-4-Cl-6-Cl | | |
| 69 | H | H | I | H | H | Cyclopropyl | 2-OMe-5-Acetyl | | 456 |
| 70 | H | H | I | H | H | Cyclopropyl | 3-Cl-5-Cl | | 452 |
| 71 | H | H | I | H | H | Cyclopropyl | 3-Me | | 398 |
| 72 | H | H | I | H | H | Cyclopropyl | 3-Me-4-Me | | |
| 73 | H | H | I | H | H | Cyclopropyl | 4-i-Pr | | 426 |
| 74 | H | H | I | H | H | Cyclopropyl | 2-CN | | |
| 75 | H | H | I | H | H | Cyclopropyl | 4-CN | | 409 |
| 76 | H | H | I | H | H | Cyclopropyl | 2-OMe | | |
| 77 | H | H | I | H | H | Cyclopropyl | 2-Me-4-Me-6-Me | | 426 |
| 78 | H | H | I | H | H | Cyclopropyl | 3,4-Methylenedioxy | | |
| 79 | H | H | I | H | H | Cyclopropyl | 2-OMe-5-OMe | | |
| 80 | H | H | I | H | H | Cyclopropyl | 3-OCF3 | | |
| 81 | H | H | I | H | H | Cyclopropyl | 2-Cl-4,5-Methylenedioxy | | 462 |
| 82 | H | H | I | Me | H | Cyclopropyl | 2-Cl-4-Cl | | 466 |
| 83 | H | H | I | Et | H | Cyclopropyl | 2-Cl-4-Cl | | 480 |
| 84 | H | H | I | H | H | Cyclopropyl | 2-Cl-4-Cl | | 452 |
| 85 | H | H | I | H | H | Cyclopropyl | 2-Cl-4-CF3 | | |
| 86 | H | H | I | H | H | Cyclopropyl | 2-Cl-4-Cl-6-Cl | | |
| 87 | H | H | I | H | H | Cyclopropyl | 2-Cl-4-CF3-6-Cl | | 520 |
| 88 | H | H | I | H | H | Cyclopropyl | 2-Cl-4-Cl-6-Cl | | 486 |
| 89 | H | H | I | Me | H | Cyclopropyl | 2-Cl-5-CF3 | | 500 |
| 90 | H | H | I | H | H | Cyclopropyl | 2-Cl-5-CF3 | | 486 |
| 91 | H | H | I | Me | H | Cyclopropyl | 4-CF3 | | 466 |
| 92 | H | H | I | n-Pr | H | Cyclopropyl | 2-Cl-4-Cl | | 494 |
| 93 | H | H | I | H | H | Cyclopropyl | 3-OPh-4-F | | 494 |
| 94 | H | H | I | H | H | Cyclopropyl | 2-Cl-6-CF3 | | 486 |
| 95 | H | H | I | H | H | Cyclopropyl | 2-F-6-CF3 | | 470 |
| 96 | H | H | I | H | H | Cyclohexyl | 2-Cl-4-Cl | | |

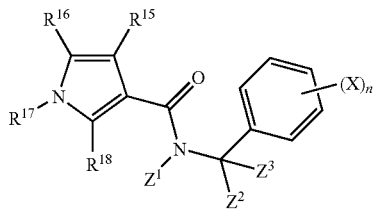

I-A⁶

| N° | R¹⁵ | R¹⁶ | R¹⁷ | R¹⁸ | Z² | Z³ | Z¹ | (X)ₙ | LogP | M + H |
|---|---|---|---|---|---|---|---|---|---|---|
| 97 | CF3 | H | Me | H | H | H | Cyclopropyl | 2-Cl-4-CF3 | | 425 |
| 98 | CF3 | H | Me | H | H | H | Cyclopropyl | 2-Cl-4-Cl | 3.88 | |
| 99 | CF3 | H | Me | H | H | H | Cyclopropyl | 2-Cl-4-Cl-6-Cl | 4.08 | |
| 100 | CF3 | H | Me | H | H | H | Cyclopropyl | 4-CF3 | 3.55 | |
| 101 | CF3 | H | Me | H | H | H | Cyclopropyl | 4-OPh | | 415 |
| 102 | CF3 | H | Me | H | H | H | Cyclopropyl | 2-OMe-5-Ac | | 395 |
| 103 | CF3 | H | Me | H | H | H | Cyclopropyl | 3-Cl-5-Cl | | 391 |
| 104 | CF3 | H | Me | H | H | H | Cyclopropyl | 3-Me | | 337 |
| 105 | CF3 | H | Me | H | H | H | Cyclopropyl | 3-Me-4-Me | | 351 |
| 106 | CF3 | H | Me | H | H | H | Cyclopropyl | 4-i-Pr | | 365 |
| 107 | CF3 | H | Me | H | H | H | Cyclopropyl | 2-CN | | |
| 108 | CF3 | H | Me | H | H | H | Cyclopropyl | 4-CN | | 348 |
| 109 | CF3 | H | Me | H | H | H | Cyclopropyl | 2-OMe | | 353 |
| 110 | CF3 | H | Me | H | H | H | Cyclopropyl | 2-Me-4-Me-6-Me | | 365 |
| 111 | CF3 | H | Me | H | H | H | Cyclopropyl | 3,4-Methylenedioxy | | 367 |

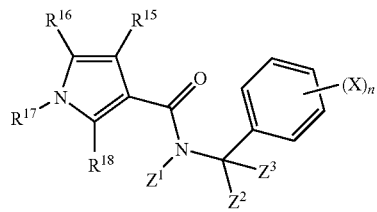

I-A⁶

| N° | R¹⁵ | R¹⁶ | R¹⁷ | R¹⁸ | Z² | Z³ | Z¹ | (X)ₙ | LogP | M + H |
|---|---|---|---|---|---|---|---|---|---|---|
| 112 | CF3 | H | Me | H | H | H | Cyclopropyl | 2-OMe-5-OMe | | 383 |
| 113 | CF3 | H | Me | H | H | H | Cyclopropyl | 3-OCF3 | | 407 |
| 114 | CF3 | H | Me | H | H | H | Cyclopropyl | 2-Cl-4, 5-Methylenedioxy | | 401 |
| 115 | CF3 | H | Me | H | Me | H | Cyclopropyl | 2-Cl-4-Cl | | 405 |
| 116 | CF3 | H | Me | H | Et | H | Cyclopropyl | 2-Cl-4-Cl | | 419 |
| 117 | CF3 | H | Me | H | Me | H | Cyclopropyl | 4-CF3 | | 405 |
| 118 | CF3 | H | Me | H | H | H | Cyclopropyl | 4-O(2-Cl-4-Cl—Ph) | | 483 |
| 119 | CF3 | H | Me | H | H | H | 3,5,5-trimethyl-cyclohexyl | 2-Cl-4-Cl-6-Cl | | |
| 120 | CF3 | H | Me | H | H | H | Cycloheptyl | 2-Cl-4-Cl-6-Cl | | |
| 121 | CF3 | H | Me | H | H | H | Cyclopropyl | 2-Cl-5-CF3 | | 425 |
| 122 | CF3 | H | Me | H | H | H | Cyclopropyl | 2-Cl-6-CF3 | | |
| 123 | CF3 | H | Me | H | CO2Me | H | Cyclopropyl | 2-Cl-5-CF3 | | 483 |
| 124 | CF3 | H | Me | H | Me | H | Cyclopropyl | 2-Cl-5-CF3 | | 439 |
| 125 | CF3 | H | Me | H | CO2Me | H | Cyclopropyl | 3-Cl-5-Cl | | 449 |
| 126 | CF3 | H | Me | H | Me | H | Cyclopropyl | 3-Cl-5-Cl | | 405 |
| 127 | CF3 | H | Me | H | H | H | Cyclopropyl | 2-Cl-4-CF3-6-Cl | | 459 |
| 128 | CF3 | H | Me | H | H | H | Cyclopropyl | 2-Cl-3-Cl-4-Cl | | 425 |
| 129 | CF3 | H | Me | H | CO2Me | H | Cyclopropyl | 2-Cl-4-Cl | | 449 |
| 130 | CF3 | H | Me | H | n-Pr | H | Cyclopropyl | 2-Cl-4-Cl | | 433 |
| 131 | CF3 | H | Me | H | CN | H | Cyclopropyl | 4-Cl | | 382 |
| 132 | CF3 | H | Me | H | CO2Me | H | Cyclopropyl | 4-Cl | | 415 |
| 133 | CF3 | H | Me | H | H | H | Cyclopropyl | 3-OPh-4-F | | 433 |
| 134 | CF3 | H | Me | H | H | H | Cyclopropyl | 2-CF3 | | 391 |
| 135 | CF3 | H | Me | H | CO2Me | H | Cyclopropyl | 2-CH2OMe | | 425 |
| 136 | CF3 | H | Me | H | H | H | Cyclopropyl | 2-Cl-6-CF3 | | 425 |
| 137 | CF3 | H | Me | H | H | H | Cyclopropyl | 2-Cl-6-Cl | | 391 |
| 138 | CF3 | H | Me | H | CO2Me | H | Cyclopropyl | 2-Cl | | 415 |
| 139 | CF3 | H | Me | H | CN | H | Cyclopropyl | 3-OPh | | 440 |
| 140 | CF3 | H | Me | H | H | H | Cyclopropyl | 2-Me-6-Me | | 351 |
| 141 | CF3 | H | Me | H | CN | H | Cyclopropyl | 2,3-(difluoro methylenedioxy) | | 428 |
| 142 | CF3 | H | Me | H | CN | H | Cyclopropyl | 2-OMe | | 378 |
| 143 | CF3 | H | Me | H | CN | H | Cyclopropyl | 2-OPh | | 440 |
| 144 | CF3 | H | Me | H | H | H | Cyclopropyl | 4-OCF3 | | 407 |
| 145 | CF3 | H | Me | H | CN | H | Cyclopropyl | 3,4-Methylenedioxy | | 392 |
| 146 | CF3 | H | Me | H | CO2Et | H | Cyclopropyl | 2-OMe-5-OMe | | 455 |

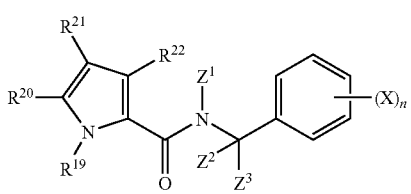

I-A⁷

| N° | R¹⁹ | R²⁰ | R²¹ | R²² | Z² | Z³ | Z¹ | (X)ₙ | LogP | M + H |
|---|---|---|---|---|---|---|---|---|---|---|
| 147 | Me | H | H | H | H | H | cyclopropyl | 2-Cl-4-Cl | | |
| 148 | Me | H | H | H | H | H | cyclopropyl | 2-Cl-4-CF3 | | |
| 149 | Me | H | H | H | H | H | cyclopropyl | 2-Cl-4-Cl-6-Cl | | |

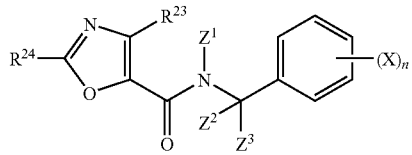

I-A⁸

| N° | R²³ | R²⁴ | Z² | Z³ | Z¹ | (X)ₙ | LogP | M + H |
|---|---|---|---|---|---|---|---|---|
| 150 | Me | H | H | H | cyclopropyl | 2-Cl-4-Cl | | 325 |
| 151 | Me | H | H | H | cyclopropyl | 2-Cl-4-CF3 | | |
| 152 | Me | Me | H | H | cyclopropyl | 2-Cl-4-Cl | | |
| 153 | Me | Me | H | H | cyclopropyl | 2-Cl-4-CF3 | | |
| 154 | Me | H | H | H | cyclopropyl | 2-Cl-4-Cl-6-Cl | | 359 |
| 155 | Me | Me | H | H | cyclopropyl | 2-Cl-4-Cl-6-Cl | | |
| 156 | Me | H | H | H | 3,5,5-trimethyl-cyclohexyl | 2-Cl-4-Cl-6-Cl | | |
| 157 | Me | H | H | H | cycloheptyl | 2-Cl-4-Cl-6-Cl | | |

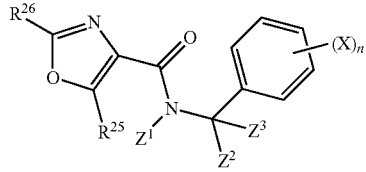

I-A⁹

| N° | R²⁵ | R²⁶ | Z² | Z³ | Z¹ | (X)ₙ | LogP | M + H |
|---|---|---|---|---|---|---|---|---|
| 158 | Me | Me | H | H | Cyclopropyl | 2-Cl-4-Cl | | 339 |
| 159 | Me | Me | H | H | Cyclopropyl | 2-Cl-4-CF3 | | |
| 160 | Me | Me | H | H | Cyclopropyl | 2-Cl-4-Cl-6-Cl | | 373 |
| 161 | Me | Me | H | H | 3,5,5-trimethyl-cyclohexyl | 2-Cl-4-Cl-6-Cl | | |
| 162 | Me | Me | H | H | cycloheptyl | 2-Cl-4-Cl-6-Cl | | |
| 163 | CF3 | Me | H | H | Cyclopropyl | 2-Cl-4-Cl | | |
| 164 | CF3 | Me | H | H | Cyclopropyl | 2-Cl-4-CF3 | | |
| 165 | CF3 | Me | H | H | Cyclopropyl | 2-Cl-4-Cl-6-Cl | | |

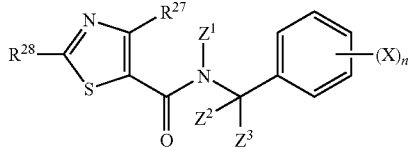

I-A¹⁰

| N° | R²⁷ | R²⁸ | Z² | Z³ | Z¹ | (X)ₙ | LogP | M + H |
|---|---|---|---|---|---|---|---|---|
| 166 | CF3 | Me | H | H | Cyclopropyl | 2-Cl-4-CF3 | | |
| 167 | CHF2 | Me | H | H | Cyclopropyl | 2-Cl-4-CF3 | | |
| 168 | CF3 | Me | H | H | Cyclopropyl | 2-Cl-4-Cl | 4.19 | |
| 169 | CHF2 | Me | H | H | Cyclopropyl | 2-Cl-4-Cl | 3.74 | |
| 170 | CF3 | Me | H | H | Cyclopropyl | 2-Cl-4-Cl-6-Cl | 4.52 | |
| 171 | CHF2 | Me | H | H | Cyclopropyl | 2-Cl-4-Cl-6-Cl | 4.1 | |
| 172 | CHF2 | Me | H | H | Cyclopropyl | 4-CF3 | 3.37 | |
| 173 | CHF2 | Me | Me | H | Cyclopropyl | 2-Cl-4-Cl | 3.9 | |
| 174 | CF3 | Me | Me | H | Cyclopropyl | 4-CF3 | | 423 |
| 175 | CHF2 | Me | Me | H | Cyclopropyl | 4-CF3 | | 405 |
| 176 | CHF2 | Me | H | H | Cyclopropyl | 4-OPh | | 415 |
| 177 | CF3 | Me | H | H | Cyclopropyl | 4-CF3 | | 409 |
| 178 | CF3 | Me | Me | H | Cyclopropyl | 2-Cl-4-Cl | | 423 |
| 179 | CHF2 | Me | H | H | Cyclopropyl | 2-OMe-5-Acetyl | | 395 |
| 180 | CHF2 | Me | H | H | Cyclopropyl | 3-Cl-5-Cl | | 391 |
| 181 | CHF2 | Me | H | H | Cyclopropyl | 3-Me | | 337 |
| 182 | CHF2 | Me | H | H | Cyclopropyl | 3-Me-4-Me | | |
| 183 | CHF2 | Me | H | H | Cyclopropyl | 4-i-Pr | | 365 |
| 184 | CHF2 | Me | H | H | Cyclopropyl | 2-CN | | |

-continued

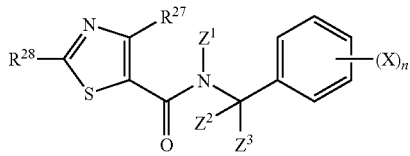

I-A¹⁰

| N° | R²⁷ | R²⁸ | Z² | Z³ | Z¹ | (X)ₙ | LogP | M + H |
|---|---|---|---|---|---|---|---|---|
| 185 | CHF2 | Me | H | H | Cyclopropyl | 4-CN | | 348 |
| 186 | CHF2 | Me | H | H | Cyclopropyl | 2-OMe | | |
| 187 | CHF2 | Me | H | H | Cyclopropyl | 2-Me-4-Me-6-Me | | 365 |
| 188 | CHF2 | Me | H | H | Cyclopropyl | 3,4-Methylenedioxy | | |
| 189 | CHF2 | Me | H | H | Cyclopropyl | 2-OMe-5-OMe | | |
| 190 | CHF2 | Me | H | H | Cyclopropyl | 3-OCF3 | | 407 |
| 191 | CHF2 | Me | H | H | Cyclopropyl | 2-Cl-4,5-Methylenedioxy | | |
| 192 | CHF2 | Me | Me | H | Cyclopropyl | 2-Cl-4-Cl | | |
| 193 | CHF2 | Me | Et | H | Cyclopropyl | 2-Cl-4-Cl | | 419 |
| 194 | CF3 | Me | H | H | Cyclopropyl | 4-OPh | | 433 |
| 195 | CF3 | Me | H | H | Cyclopropyl | 4-O(2-Cl-4-Cl—Ph) | | 501 |
| 196 | CHF2 | Me | H | H | Cyclopropyl | 4-O(2-Cl-4-Cl—Ph) | | 483 |
| 197 | CF3 | Me | H | H | 3,5,5-trimethyl-cyclohexyl | 2-Cl-4-Cl-6-Cl | | |
| 198 | CHF2 | Me | H | H | Cycloheptyl | 2-Cl-4-Cl-6-Cl | | |
| 199 | CF3 | Me | H | H | 3,5,5-trimethyl-cyclohexyl | 2-Cl-4-Cl-6-Cl | | |
| 200 | CHF2 | Me | H | H | Cycloheptyl | 2-Cl-4-Cl-6-Cl | | |
| 201 | CHF2 | Me | H | H | Cyclopropyl | 2-Cl-5-CF3 | | |
| 202 | CHF2 | Me | H | H | Cyclopropyl | 2-Cl-6-CF3 | | |
| 203 | CF3 | Me | H | H | Cyclopropyl | 2-Cl-5-CF3 | | |
| 204 | CF3 | Me | H | H | Cyclopropyl | 2-Cl-6-CF3 | | |
| 205 | CF3 | Me | H | H | Cyclopropyl | 3-OPh-4-F | | 451 |
| 206 | CHF2 | Me | Me | H | Cyclopropyl | 2-Cl-5-CF3 | | 439 |
| 207 | CHF2 | Me | H | H | Cyclopropyl | 2-Cl-5-CF3 | | 425 |
| 208 | CHF2 | Me | H | H | Cyclopropyl | 2-Cl-3-Cl-4-Cl | | 425 |
| 209 | CHF2 | Me | CN | H | Cyclopropyl | 2-Cl-4-Cl | 3.61 | |
| 210 | CHF2 | Me | n-Pr | H | Cyclopropyl | 2-Cl-4-Cl | | 433 |
| 211 | CHF2 | Me | H | H | Cyclopropyl | 3-OPh-4-F | | 433 |
| 212 | CHF2 | Me | CN | H | Cyclopropyl | 2-CF3 | | 416 |
| 213 | CHF2 | Me | CN | H | Cyclopropyl | 2-Cl-6-Cl | 3.14 | |
| 214 | CHF2 | Me | H | H | Cyclopropyl | 2-Cl-6-Cl | | 391 |
| 215 | CHF2 | Me | H | H | Cyclopropyl | 4-OCF3 | | 407 |
| 216 | CF3 | Me | H | H | Cyclopentyl | 2-Cl-4-Cl-6-Cl | | |
| 217 | CF3 | Me | H | H | 2-Me-cyclopropyl | 2-Cl-6-Cl | | |
| 218 | CF3 | Me | H | H | 2-F-cyclopropyl | 2-Cl-6-Cl | | |
| 219 | CF3 | Me | H | H | 1-Me-cyclopropyl | 2-Cl-6-Cl | | |
| 220 | CHF2 | Me | H | H | Cyclopentyl | 2-Cl-4-Cl-6-Cl | | |
| 221 | CHF2 | Me | H | H | 2-Me-cyclopropyl | 2-Cl-6-Cl | | |
| 222 | CHF2 | Me | H | H | 2-F-cyclopropyl | 2-Cl-6-Cl | | |
| 223 | CHF2 | Me | H | H | 1-Me-cyclopropyl | 2-Cl-6-Cl | | |
| 224 | CHF2 | Me | H | H | 2-F-cyclopropyl | 2-Cl-4-Cl-6-Cl | | |
| 225 | CHF2 | Me | H | H | 1-Me-cyclopropyl | 2-Cl-4-Cl-6-Cl | | |

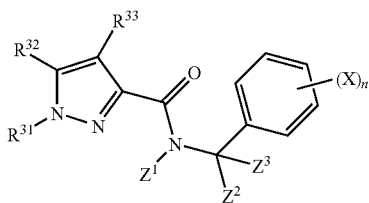

I-A¹²

| N° | R³¹ | R³² | R³³ | Z² | Z³ | Z¹ | (X)ₙ | LogP | M + H |
|---|---|---|---|---|---|---|---|---|---|
| 226 | Me | Me | H | H | H | Cyclopropyl | 2-Cl-4-Cl | | 338 |
| 227 | Me | Me | H | H | H | Cyclopropyl | 2-Cl-4-CF3 | | |
| 228 | Me | Me | H | H | H | Cyclopropyl | 2-Cl-4-Cl-6-Cl | | 372 |
| 229 | Me | Me | H | H | H | Cyclopropyl | 2-Cl-6-CF3 | | |
| 230 | Me | Me | H | Me | H | Cyclopropyl | 2-Cl-4-Cl | | |
| 231 | Me | Me | H | H | H | Cyclopentyl | 2-Cl-4-Cl | | |

-continued

I-A¹²

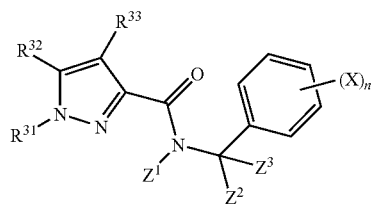

| N° | R³¹ | R³² | R³³ | Z² | Z³ | Z¹ | (X)ₙ | LogP | M + H |
|---|---|---|---|---|---|---|---|---|---|
| 232 | Me | Me | H | H | H | Cyclohexyl | 2-Cl-4-Cl | | |
| 233 | Me | Me | H | H | H | Cyclopentyl | 2-Cl-4-Cl-6-Cl | | |
| 234 | Me | Me | H | H | H | Cyclohexyl | 2-Cl-4-Cl-6-Cl | | |

I-A¹³

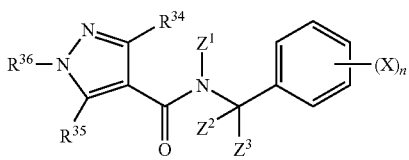

| N° | R³⁴ | R³⁵ | R³⁶ | Z² | Z³ | Z¹ | (X)ₙ | LogP | M + H |
|---|---|---|---|---|---|---|---|---|---|
| 235 | Me | F | Me | H | H | Cyclopropyl | 2-Cl-4-CF3 | | 390 |
| 236 | Me | F | Me | H | H | Cyclopropyl | 2-Cl-4-Cl | 3.04 | |
| 237 | Me | F | Me | H | H | Cyclopropyl | 4-CF3 | 2.8 | |
| 238 | Me | F | Me | H | H | Cyclopropyl | 2-Cl-4-Cl-6-Cl | 3.32 | |
| 239 | Me | F | Me | H | H | Cyclopropyl | 4-OPh | | 380 |
| 240 | CHF2 | H | Me | H | H | Cyclopropyl | 2-Cl-4-CF3 | | 408 |
| 241 | CHF2 | H | Me | H | H | Cyclopropyl | 2-Cl-4-Cl | 3.27 | |
| 242 | CHF2 | H | Me | H | H | Cyclopropyl | 4-CF3 | 2.98 | |
| 243 | CHF2 | H | Me | H | H | Cyclopropyl | 2-Cl-4-Cl-6-Cl | 3.46 | |
| 244 | CHF2 | H | Me | H | H | Cyclopropyl | 4-OPh | 3.37 | |
| 245 | CHF2 | H | Me | Me | H | Cyclopropyl | 2-Cl-4-Cl | 3.31 | |
| 246 | CHF2 | H | Me | Me | H | Cyclopropyl | 4-CF3 | 3.27 | |
| 247 | OMe | H | Me | H | H | Cyclopropyl | 2-Cl-4-CF3 | | 388 |
| 248 | CF3 | H | Me | H | H | Cyclopropyl | 2-Cl-4-CF3 | | 426 |
| 249 | OEt | H | Me | H | H | Cyclopropyl | 2-Cl-4-CF3 | | |
| 250 | I | H | Me | H | H | Cyclopropyl | 2-Cl-4-CF3 | | 484 |
| 251 | OMe | H | Me | H | H | Cyclopropyl | 2-Cl-4-Cl | 2.81 | |
| 252 | CF3 | H | Me | H | H | Cyclopropyl | 2-Cl-4-Cl | 3.58 | |
| 253 | OEt | H | Me | H | H | Cyclopropyl | 2-Cl-4-Cl | 3.22 | |
| 254 | I | H | Me | H | H | Cyclopropyl | 2-Cl-4-Cl | 3.15 | |
| 255 | OMe | H | Me | H | H | Cyclopropyl | 2-Cl-4-Cl-6-Cl | 2.97 | |
| 256 | CF3 | H | Me | H | H | Cyclopropyl | 2-Cl-4-Cl-6-Cl | 3.78 | |
| 257 | OEt | H | Me | H | H | Cyclopropyl | 2-Cl-4-Cl-6-Cl | 3.35 | |
| 258 | I | H | Me | H | H | Cyclopropyl | 2-Cl-4-Cl-6-Cl | 3.34 | |
| 259 | OMe | H | Me | H | H | Cyclopropyl | 4-CF3 | 2.61 | |
| 260 | CF3 | H | Me | H | H | Cyclopropyl | 4-CF3 | 3.29 | |
| 261 | OEt | H | Me | H | H | Cyclopropyl | 4-CF3 | 2.92 | |
| 262 | I | H | Me | H | H | Cyclopropyl | 4-CF3 | 2.92 | |
| 263 | Me | F | Me | Me | H | Cyclopropyl | 2-Cl-4-Cl | 3.19 | |
| 264 | OMe | H | Me | Me | H | Cyclopropyl | 2-Cl-4-Cl | 2.83 | |
| 265 | OEt | H | Me | Me | H | Cyclopropyl | 2-Cl-4-Cl | 3.19 | |
| 266 | I | H | Me | Me | H | Cyclopropyl | 2-Cl-4-Cl | 3.22 | |
| 267 | OEt | H | Me | Me | H | Cyclopropyl | 4-CF3 | | 382 |
| 268 | OMe | H | Me | H | H | Cyclopropyl | 4-OPh | | 378 |
| 269 | CF3 | H | Me | H | H | Cyclopropyl | 4-OPh | | 416 |
| 270 | OEt | H | Me | H | H | Cyclopropyl | 4-OPh | | 392 |
| 271 | OMe | H | Me | H | H | Cyclopropyl | 4-O(2-Cl-4-Cl—Ph) | | 446 |
| 272 | CF3 | H | Me | H | H | Cyclopropyl | 4-O(2-Cl-4-Cl—Ph) | | 484 |
| 273 | OEt | H | Me | H | H | Cyclopropyl | 4-O(2-Cl-4-Cl—Ph) | | 460 |
| 274 | Me | F | Me | H | H | Cyclopropyl | 2-Cl-3-Cl-4-Cl | | 390 |
| 275 | CHF2 | H | Me | H | H | Cyclopropyl | 2-Cl-3-Cl-4-Cl | | 408 |
| 276 | CF3 | H | Me | Me | H | Cyclopropyl | 2-Cl-4-Cl | | 406 |
| 277 | Me | F | Me | H | H | Cyclopropyl | 2-OMe-5-Ac | | |
| 278 | CHF2 | H | Me | H | H | Cyclopropyl | 2-OMe-5-Ac | | 378 |
| 279 | OMe | H | Me | H | H | Cyclopropyl | 2-OMe-5-Ac | | 358 |
| 280 | Me | F | Me | H | H | Cyclopropyl | 3-Cl-5-Cl | | 356 |
| 281 | CHF2 | H | Me | H | H | Cyclopropyl | 3-Cl-5-Cl | | 374 |

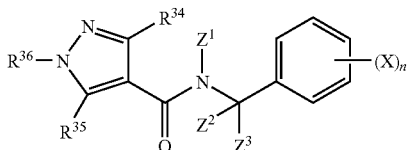

I-A[13]

| N° | R34 | R35 | R36 | Z2 | Z3 | Z1 | (X)n | LogP | M + H |
|---|---|---|---|---|---|---|---|---|---|
| 282 | OMe | H | Me | H | H | Cyclopropyl | 3-Cl-5-Cl | | 354 |
| 283 | Me | F | Me | H | H | Cyclopropyl | 3-Me | | 302 |
| 284 | CHF2 | H | Me | H | H | Cyclopropyl | 3-Me | | 320 |
| 285 | OMe | H | Me | H | H | Cyclopropyl | 3-Me | | 300 |
| 286 | Me | F | Me | H | H | Cyclopropyl | 3-Me-4-Me | | 316 |
| 287 | CHF2 | H | Me | H | H | Cyclopropyl | 3-Me-4-Me | | 334 |
| 288 | OMe | H | Me | H | H | Cyclopropyl | 3-Me-4-Me | | |
| 289 | Me | F | Me | H | H | Cyclopropyl | 4-i-Pr | | 330 |
| 290 | CHF2 | H | Me | H | H | Cyclopropyl | 4-i-Pr | | |
| 291 | OMe | H | Me | H | H | Cyclopropyl | 4-i-Pr | | |
| 292 | Me | F | Me | H | H | Cyclopropyl | 2-CN | | |
| 293 | CHF2 | H | Me | H | H | Cyclopropyl | 2-CN | | |
| 294 | OMe | H | Me | H | H | Cyclopropyl | 2-CN | | |
| 295 | Me | F | Me | H | H | Cyclopropyl | 4-CN | | 313 |
| 296 | CHF2 | H | Me | H | H | Cyclopropyl | 4-CN | | |
| 297 | OMe | H | Me | H | H | Cyclopropyl | 4-CN | | 311 |
| 298 | Me | F | Me | H | H | Cyclopropyl | 2-OMe | | 318 |
| 299 | CHF2 | H | Me | H | H | Cyclopropyl | 2-OMe | | 336 |
| 300 | OMe | H | Me | H | H | Cyclopropyl | 2-OMe | | 316 |
| 301 | Me | F | Me | H | H | Cyclopropyl | 2-Me-4-Me-6-Me | | 330 |
| 302 | CHF2 | H | Me | H | H | Cyclopropyl | 2-Me-4-Me-6-Me | | 348 |
| 303 | OMe | H | Me | H | H | Cyclopropyl | 2-Me-4-Me-6-Me | | 328 |
| 304 | Me | F | Me | H | H | Cyclopropyl | 3,4-Methylenedioxy | | 332 |
| 305 | CHF2 | H | Me | H | H | Cyclopropyl | 3,4-Methylenedioxy | | 350 |
| 306 | OMe | H | Me | H | H | Cyclopropyl | 3,4-Methylenedioxy | | 330 |
| 307 | Me | F | Me | H | H | Cyclopropyl | 2-OMe-5-OMe | | 348 |
| 308 | Me | F | Me | H | H | Cyclopropyl | 3-OCF3 | | 372 |
| 309 | CHF2 | H | Me | H | H | Cyclopropyl | 2-OMe-5-OMe | | 366 |
| 310 | CHF2 | H | Me | H | H | Cyclopropyl | 3-OCF3 | | 390 |
| 311 | OMe | H | Me | H | H | Cyclopropyl | 2-OMe-5-OMe | | 346 |
| 312 | OMe | H | Me | H | H | Cyclopropyl | 3-OCF3 | | 370 |
| 313 | Me | F | Me | H | H | Cyclopropyl | 2-Cl-4,5-Methylenedioxy | | 366 |
| 314 | Me | F | Me | Me | H | Cyclopropyl | 4-Cl-6-Cl | | |
| 315 | Me | F | Me | Me | H | Cyclopropyl | 4-Cl-6-Cl | | |
| 316 | CHF2 | H | Me | H | H | Cyclopropyl | 2-Cl-4,5-Methylenedioxy | | |
| 317 | CHF2 | H | Me | Me | H | Cyclopropyl | 4-Cl-6-Cl | | |
| 318 | CHF2 | H | Me | Me | H | Cyclopropyl | 4-Cl-6-Cl | | |
| 319 | OMe | H | Me | H | H | Cyclopropyl | 2-Cl-4,5-Methylenedioxy | | 364 |
| 320 | OMe | H | Me | Me | H | Cyclopropyl | 4-Cl-6-Cl | | |
| 321 | OMe | H | Me | Me | H | Cyclopropyl | 4-Cl-6-Cl | | |
| 322 | Et | F | Me | H | H | Cyclopropyl | 2-Cl-4-Cl | | 370 |
| 323 | Et | F | Me | H | H | Cyclopropyl | 2-Cl-4-CF3 | | 404 |
| 324 | Me | H | Me | H | H | Cyclopropyl | 2-Cl-4-Cl | | 338 |
| 325 | Me | H | Me | H | H | Cyclopropyl | 2-Cl-4-CF3 | | |
| 326 | H | H | H | H | H | Cyclopropyl | 2-Cl-4-Cl | | |
| 327 | H | H | H | H | H | Cyclopropyl | 2-Cl-4-CF3 | | |
| 328 | Et | F | Me | H | H | Cyclopropyl | 2-Cl-4-Cl-6-Cl | | 404 |
| 329 | Me | H | Me | H | H | Cyclopropyl | 2-Cl-4-Cl-6-Cl | | 372 |
| 330 | H | H | H | H | H | Cyclopropyl | 2-Cl-4-Cl-6-Cl | | |
| 331 | CF3 | H | Me | H | H | Cyclopropyl | 2-OMe-5-Ac | | 396 |
| 332 | CF3 | H | Me | H | H | Cyclopropyl | 3-Cl-5-Cl | | 392 |
| 333 | CF3 | H | Me | H | H | Cyclopropyl | 3-Me | | 338 |
| 334 | CF3 | H | Me | H | H | Cyclopropyl | 3-Me-4-Me | | |
| 335 | CF3 | H | Me | H | H | Cyclopropyl | 4-i-Pr | | 366 |
| 336 | CF3 | H | Me | H | H | Cyclopropyl | 2-CN | | |
| 337 | CF3 | H | Me | H | H | Cyclopropyl | 4-CN | | 349 |
| 338 | CF3 | H | Me | H | H | Cyclopropyl | 2-OMe | | 353 |
| 339 | CF3 | H | Me | H | H | Cyclopropyl | 2-Me-4-Me-6-Me | | |
| 340 | Me | F | Me | H | H | Cyclopropyl | 2-Cl-4-Cl-6-Cl | | |
| 341 | Me | F | Me | H | H | 2-F-cyclopropyl | 2-Cl-4-Cl-6-Cl | | |
| 342 | Me | F | Me | H | H | 1-Me-cyclopropyl | 2-Cl-4-Cl-6-Cl | | |
| 343 | Me | F | Me | H | H | Cyclopropyl | 2-Cl-6-CF3 | | |
| 344 | CF3 | H | Me | H | H | Cyclopropyl | 3,4-Methylenedioxy | | |
| 345 | CF3 | H | Me | H | H | Cyclopropyl | 2-OMe-5-OMe | | |
| 346 | CF3 | H | Me | H | H | Cyclopropyl | 3-OCF3 | | 407 |
| 347 | CF3 | H | Me | H | H | Cyclopropyl | 2-Cl-4,5-Methylenedioxy | | 402 |
| 348 | CF3 | H | Me | Me | H | Cyclopropyl | 4-Cl-6-Cl | | |
| 349 | CF3 | H | Me | Me | H | Cyclopropyl | 4-Cl-6-Cl | | |

-continued

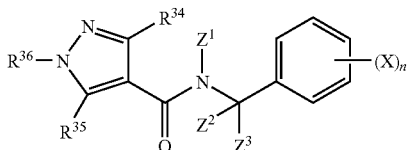

I-A13

| N° | R34 | R35 | R36 | Z2 | Z3 | Z1 | (X)n | LogP | M + H |
|---|---|---|---|---|---|---|---|---|---|
| 350 | Me | F | Me | CO2Me | H | Cyclopropyl | 3-Cl-5-Cl | | |
| 351 | Me | F | Me | H | H | Cyclopropyl | 2-Cl-4-CF3-6-Cl | | 424 |
| 352 | Me | F | Me | H | H | Cyclopropyl | 2-Cl-6-Cl | | 356 |
| 353 | CHF2 | H | Me | H | H | Cyclopropyl | 2-Cl-4-CF3-6-Cl | | 442 |
| 354 | CHF2 | H | Me | H | H | Cyclopropyl | 2-Cl-6-Cl | | 374 |
| 355 | Me | F | Me | Me | H | Cyclopropyl | 4-CF3 | | 370 |
| 356 | OMe | H | Me | Me | H | Cyclopropyl | 4-CF3 | | 368 |
| 357 | CF3 | H | Me | Me | H | Cyclopropyl | 4-CF3 | | 406 |
| 358 | Me | F | Me | H | H | Cyclopropyl | 4-O(2-Cl-4-Cl—Ph) | | 448 |
| 359 | Me | F | Me | H | H | Cyclopropyl | 2-OMe-5-Ac | | 360 |
| 360 | Me | F | Me | H | H | 3,5,5-trimethyl-cyclohexyl | 2-Cl-4-Cl-6-Cl | | |
| 361 | CHF2 | H | Me | H | H | 3,5,5-trimethyl-cyclohexyl | 2-Cl-4-Cl-6-Cl | | |
| 362 | OMe | H | Me | H | H | 3,5,5-trimethyl-cyclohexyl | 2-Cl-4-Cl-6-Cl | | |
| 363 | Me | F | Me | H | H | Cycloheptyl | 2-Cl-4-Cl-6-Cl | | |
| 364 | CHF2 | H | Me | H | H | Cycloheptyl | 2-Cl-4-Cl-6-Cl | | |
| 365 | OMe | H | Me | H | H | Cycloheptyl | 2-Cl-4-Cl-6-Cl | | |
| 366 | Me | F | Me | H | H | Cyclopropyl | 2-Cl-5-CF3 | | |
| 367 | CHF2 | H | Me | H | H | Cyclopropyl | 2-Cl-5-CF3 | | |
| 368 | OMe | H | Me | H | H | Cyclopropyl | 2-Cl-5-CF3 | | |
| 369 | Me | F | Me | H | H | Cyclopropyl | 2-Cl-6-CF3 | | |
| 370 | CHF2 | H | Me | H | H | Cyclopropyl | 2-Cl-6-CF3 | | |
| 371 | OMe | H | Me | H | H | Cyclopropyl | 2-Cl-6-CF3 | | |
| 372 | Me | H | Me | H | H | Cyclopropyl | 2-Cl-5-CF3 | | 372 |
| 373 | Me | H | Me | Me | H | Cyclopropyl | 2-Cl-4-Cl | | 352 |
| 374 | Me | H | Me | H | H | Cyclopropyl | 3-OPh-4-F | | 380 |
| 375 | Me | H | Me | H | H | Cyclopropyl | 2-Cl-6-CF3 | | 372 |
| 376 | Me | H | Me | H | H | Cyclopropyl | 2-Cl-6-Cl | | 338 |
| 377 | Me | H | Me | H | H | Cyclopropyl | 2-Me-4-Me-6-Me | | 312 |
| 378 | Me | F | Me | H | H | Cyclopropyl | 2-Br | | 366 |
| 379 | Me | F | Me | Me | H | Cyclopropyl | 2-CF3 | | 370 |
| 380 | Me | F | Me | H | H | Cyclopropyl | 2-CF3 | | 356 |
| 381 | Me | F | Me | H | H | Cyclopropyl | 2-CF3-5-CF3 | | 424 |
| 382 | Me | F | Me | CO2Me | H | Cyclopropyl | 2-CH2OMe | | 390 |
| 383 | Me | F | Me | CO2Me | H | Cyclopropyl | 2-Cl | 2.57 | |
| 384 | Me | F | Me | H | H | Cyclopropyl | 2-Cl | | 322 |
| 385 | Me | F | Me | CN | H | Cyclopropyl | 2-Cl-4-Cl | 3.15 | |
| 386 | Me | F | Me | Et | H | Cyclopropyl | 2-Cl-4-Cl | 3.53 | |
| 387 | Me | F | Me | n-Pr | H | Cyclopropyl | 2-Cl-4-Cl | | 398 |
| 388 | Me | F | Me | n-Bu | H | Cyclopropyl | 2-Cl-4-Cl | | 412 |
| 389 | Me | F | Me | CO2Me | H | Cyclopropyl | 2-Cl-4-Cl | | 414 |
| 390 | Me | F | Me | Me | H | Cyclopropyl | 2-Cl-5-CF3 | | 404 |
| 391 | Me | F | Me | CO2Me | H | Cyclopropyl | 2-Cl-5-CF3 | | 448 |
| 392 | CHF2 | H | Me | H | H | 2-Me-cyclopropyl | 2-Cl-6-Cl | | |
| 393 | CHF2 | H | Me | H | H | 2-F-cyclopropyl | 2-Cl-6-Cl | | |
| 394 | CHF2 | H | Me | H | H | 1-Me-cyclopropyl | 2-Cl-6-Cl | | |
| 395 | Me | F | Me | H | H | Cyclopropyl | 2-Cl-5-CF3 | | 390 |
| 396 | Me | F | Me | H | H | Cyclopropyl | 2-Cl-5-Cl | | 356 |
| 397 | Me | F | Me | H | H | Cyclopropyl | 2-Cl-6-CF3 | | 390 |
| 398 | Me | F | Me | CN | H | Cyclopropyl | 2-CN | | 338 |
| 399 | Me | F | Me | H | H | Cyclopropyl | 2-Cyclohexyl | | 370 |
| 400 | Me | F | Me | H | H | Cyclopropyl | 2-F-4-Br | | 384 |
| 401 | Me | F | Me | H | H | Cyclopropyl | 2-F-4-O-(3-Cl-4-F—Ph) | | 434 |
| 402 | Me | F | Me | H | H | Cyclopropyl | 2-I | | 414 |
| 403 | Me | F | Me | H | H | Cyclopropyl | 2-Me-5-Me | | 316 |
| 404 | Me | F | Me | CN | H | Cyclopropyl | 2-OMe | | 343 |
| 405 | Me | F | Me | H | H | Cyclopropyl | 2-OMe-5-C(NOEt)Me | | 389 |
| 406 | Me | F | Me | H | H | Cyclopropyl | 2-OMe-5-C(NOEt)Me | | 403 |
| 407 | Me | F | Me | H | H | Cyclopropyl | 2-OMe-5-C(NOiBu)Me | | 431 |
| 408 | Me | F | Me | H | H | Cyclopropyl | 2-OMe-5-C(NOiPr)Me | | 417 |
| 409 | Me | F | Me | H | H | Cyclopropyl | 2-OMe-5-C(NOtBu)Me | | 431 |
| 410 | Me | F | Me | CO2Et | H | Cyclopropyl | 2-OMe-5-OMe | | 420 |
| 411 | Me | F | Me | CN | H | Cyclopropyl | 2-OPh | | 405 |
| 412 | Me | F | Me | H | H | Cyclopropyl | 3-Br | 2.66 | |
| 413 | Me | F | Me | H | H | Cyclopropyl | 3-Br-5-Br | | 444 |
| 414 | Me | F | Me | Me | H | Cyclopropyl | 3-Cl-5-Cl | | 370 |

-continued

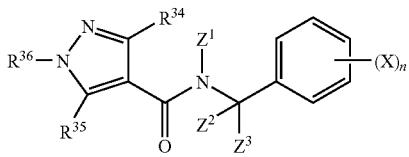

I-A¹³

| N° | R³⁴ | R³⁵ | R³⁶ | Z² | Z³ | Z¹ | (X)ₙ | LogP | M + H |
|---|---|---|---|---|---|---|---|---|---|
| 415 | Me | F | Me | Et | H | Cyclopropyl | 3-Cl-5-Cl | | 384 |
| 416 | Me | F | Me | H | H | Cyclopentyl | 2-Cl-4-Cl-6-Cl | | |
| 417 | Me | F | Me | H | H | 2-Me-cyclopropyl | 2-Cl-6-Cl | | 369 |
| 418 | Me | F | Me | H | H | 2-F-cyclopropyl | 2-Cl-6-Cl | | |
| 419 | Me | F | Me | H | H | 1-Me-cyclopropyl | 2-Cl-6-Cl | | |
| 420 | Me | F | Me | Me | H | Cyclopropyl | 3-OPh-4-F | | 412 |
| 421 | Me | F | Me | H | H | Cyclopropyl | 3-OPh-4-F | | 398 |
| 422 | Me | F | Me | H | H | Cyclopropyl | 4-Br | 2.67 | |
| 423 | Me | F | Me | Et | H | Cyclopropyl | 4-CF3 | | 384 |
| 424 | Me | F | Me | n-Bu | H | Cyclopropyl | 4-CF3 | | 412 |
| 425 | Me | F | Me | H | H | Cyclopropyl | 4-CH2OH | | 318 |
| 426 | Me | F | Me | CO2Me | H | Cyclopropyl | 4-Cl | | 380 |
| 427 | Me | F | Me | CN | H | Cyclopropyl | 4-Cl | | 347 |
| 428 | Me | F | Me | H | H | Cyclopropyl | 4-CHNOiPr | | 373 |
| 429 | Me | F | Me | CO2Et | H | Cyclopropyl | 4-i-Bu | | 416 |
| 430 | Me | F | Me | H | H | Cyclopropyl | 4-O-(3-Cl-4-F—Ph) | | 416 |
| 431 | Me | F | Me | H | H | Cyclopropyl | 4-O-(4-CF3-Ph) | | 448 |
| 432 | Me | F | Me | H | H | Cyclopropyl | 4-O-(4-Cl-Ph) | | 414 |
| 433 | Me | F | Me | H | H | Cyclopropyl | 4-OCF3 | | 372 |
| 434 | Me | F | Et | H | H | Cyclopropyl | 2-Cl-4-CF3 | | 404 |
| 435 | Me | F | Et | H | H | Cyclopropyl | 2-Cl-4-Cl | | 370 |
| 436 | Me | F | Et | Me | H | Cyclopropyl | 2-Cl-4-Cl | | 384 |
| 437 | Me | F | Et | H | H | Cyclopropyl | 2-Cl-4-Cl-6-Cl | | 404 |
| 438 | Me | F | Et | H | H | Cyclopropyl | 2-Cl-6-CF3 | | 404 |
| 439 | Me | F | Et | H | H | Cyclopropyl | 2-Cl-6-Cl | | 370 |
| 440 | Me | F | Et | Me | H | Cyclopropyl | 4-CF3 | | 384 |
| 441 | OMe | H | Me | CO2Me | H | Cyclopropyl | 2-CH2OMe | | 388 |
| 442 | OMe | H | Me | CO2Me | H | Cyclopropyl | 2-Cl | | 378 |
| 443 | OMe | H | Me | H | H | Cyclopropyl | 2-Cl-3-Cl-4-Cl | | 388 |
| 444 | OMe | H | Me | CO2Me | H | Cyclopropyl | 2-Cl-4-Cl | | 412 |
| 445 | OMe | H | Me | Et | H | Cyclopropyl | 2-Cl-4-Cl | | 382 |
| 446 | OMe | H | Me | n-Pr | H | Cyclopropyl | 2-Cl-4-Cl | | 396 |
| 447 | OMe | H | Me | CO2Me | H | Cyclopropyl | 2-Cl-5-CF3 | | 446 |
| 448 | OMe | H | Me | Me | H | Cyclopropyl | 2-Cl-5-CF3 | | 402 |
| 449 | OMe | H | Me | H | H | Cyclopropyl | 2-Cl-5-CF3 | | 388 |
| 450 | OMe | H | Me | H | H | Cyclopropyl | 2-Cl-6-CF3 | | 388 |
| 451 | OMe | H | Me | CN | H | Cyclopropyl | 2-Cl-6-Cl | | 379 |
| 452 | OMe | H | Me | H | H | Cyclopropyl | 2-Cl-6-Cl | | 354 |
| 453 | OMe | H | Me | CN | H | Cyclopropyl | 2-OCF2O-3-OCF2O | | 391 |
| 454 | OMe | H | Me | CN | H | Cyclopropyl | 2-OMe | | 341 |
| 455 | OMe | H | Me | CO2Et | H | Cyclopropyl | 2-OMe-5-OMe | | 418 |
| 456 | OMe | H | Me | CN | H | Cyclopropyl | 2-OPh | | 403 |
| 457 | OMe | H | Me | CO2Me | H | Cyclopropyl | 3-Cl-5-Cl | | 412 |
| 458 | OMe | H | Me | CN | H | Cyclopropyl | 3-OCH2O-4-OCH2O | | 355 |
| 459 | OMe | H | Me | CN | H | Cyclopropyl | 3-OPh | | 403 |
| 460 | OMe | H | Me | H | H | Cyclopropyl | 3-OPh-4-F | | 396 |
| 461 | OMe | H | Me | CN | H | Cyclopropyl | 4-Cl | | 345 |
| 462 | OMe | H | Me | CO2Me | H | Cyclopropyl | 4-Cl | | 378 |
| 463 | OMe | H | Me | H | H | Cyclopropyl | 4-OCF3 | | 370 |
| 464 | H | Cl | Me | Me | H | Cyclopropyl | 2-Cl-4-Cl | | 372 |
| 465 | H | Cl | Me | H | H | Cyclopropyl | 2-Cl-4-Cl | | 358 |
| 466 | H | Cl | Me | H | H | Cyclopropyl | 2-Cl-4-Cl-6-Cl | | 392 |
| 467 | CHF2 | H | CH2OMe | H | H | Cyclopropyl | 2-Cl-6-CF3 | | 438 |
| 468 | CF3 | H | Me | n-Bu | H | Cyclopropyl | 4-CF3 | | 430 |
| 469 | CF3 | H | Me | CN | H | Cyclopropyl | 2-CF3 | | 417 |
| 470 | CF3 | H | Me | H | H | Cyclopropyl | 2-CF3 | | 392 |
| 471 | CF3 | H | Me | CO2Me | H | Cyclopropyl | 2-CH2OMe | | 426 |
| 472 | CF3 | H | Me | CO2Me | H | Cyclopropyl | 2-Cl | | 416 |
| 473 | CF3 | H | Me | H | H | Cyclopropyl | 2-Cl-3-Cl-4-Cl | | |
| 474 | CF3 | H | Me | H | H | Cyclopropyl | 2-Cl-4-CF3-6-Cl | | 460 |
| 475 | CF3 | H | Me | CO2Me | H | Cyclopropyl | 2-Cl-4-Cl | | 450 |
| 476 | CF3 | H | Me | Et | H | Cyclopropyl | 2-Cl-4-Cl | | 420 |
| 477 | CF3 | H | Me | n-Pr | H | Cyclopropyl | 2-Cl-4-Cl | | 434 |
| 478 | CF3 | F | Me | H | H | Cyclopropyl | 2-Cl-4-CF3 | | 444 |
| 479 | CF3 | F | Me | H | H | Cyclopropyl | 2-Cl-4-Cl | | 410 |
| 480 | CF3 | F | Me | Me | H | Cyclopropyl | 2-Cl-4-Cl | | 424 |
| 481 | CF3 | F | Me | H | H | Cyclopropyl | 2-Cl-4-Cl-6-Cl | | |
| 482 | CHF2 | H | Me | H | H | Cyclopropyl | 2-CF3-5-CF3 | | 442 |

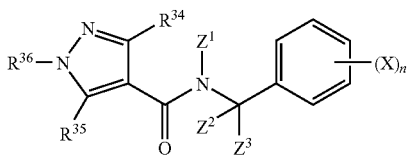

I-A¹³

| N° | R³⁴ | R³⁵ | R³⁶ | Z² | Z³ | Z¹ | (X)ₙ | LogP | M + H |
|---|---|---|---|---|---|---|---|---|---|
| 483 | CHF2 | H | Me | CO2Me | H | Cyclopropyl | 2-CH2OMe | | 408 |
| 484 | CHF2 | H | Me | CO2Me | H | Cyclopropyl | 2-Cl | | 398 |
| 485 | CHF2 | H | Me | H | H | Cyclopropyl | 2-Cl | | 340 |
| 486 | CHF2 | H | Me | CN | H | Cyclopropyl | 2-Cl-4-Cl | | |
| 487 | CHF2 | H | Me | H | H | Cyclopropyl | 4-O-(3-Cl-4-F—Ph) | | 434 |
| 488 | CHF2 | H | Me | H | H | Cyclopropyl | 4-O-(4-CF3-Ph) | | 466 |
| 489 | CHF2 | H | Me | H | H | Cyclopropyl | 4-O-(4-Cl-Ph) | | 432 |
| 490 | CHF2 | H | Me | H | H | Cyclopropyl | 2-F-4-Br | | |
| 491 | CHF2 | H | Me | H | H | Cyclopropyl | 2-F-4-O-(3-Cl-4-F—Ph) | | 452 |
| 492 | CHF2 | H | Me | CO2Et | H | Cyclopropyl | 2-OMe-5-OMe | | 438 |
| 493 | CHF2 | H | Me | Me | Me | Cyclopropyl | 2-Cl-4-Cl | | |
| 494 | CHF2 | H | Me | Me | Me | Cyclopropyl | 4-CF3 | | |
| 495 | CHF2 | H | Me | Me | Me | Cyclopropyl | 2-CF3 | | |
| 496 | Me | F | Me | Me | Me | Cyclopropyl | 2-Cl-4-Cl | | |
| 497 | Me | F | Me | Me | Me | Cyclopropyl | 4-CF3 | | |
| 498 | Me | F | Me | Me | Me | Cyclopropyl | 2-CF3 | | |
| 499 | CHF2 | H | Me | OMe | H | Cyclopropyl | 2-Cl-4-Cl | | |
| 500 | Me | F | Me | OMe | H | Cyclopropyl | 2-Cl-4-Cl | 2.96 | |
| 501 | CHF2 | H | Me | OEt | H | Cyclopropyl | 2-Cl-4-Cl | | |
| 502 | Me | F | Me | OEt | H | Cyclopropyl | 2-Cl-4-Cl | | |

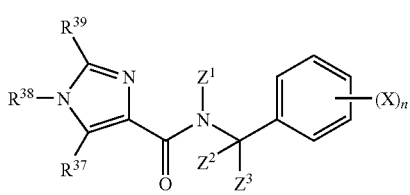

I-A¹⁴

| N° | R³⁷ | R³⁸ | R³⁹ | Z² | Z³ | Z¹ | (X)ₙ | LogP | M + H |
|---|---|---|---|---|---|---|---|---|---|
| 503 | H | Me | H | H | H | cyclopropyl | 2-Cl-4-Cl-6-Cl | 2.40 | |
| 504 | H | Me | H | H | H | cyclopropyl | 2-Cl-4-CF3 | | |
| 505 | H | Me | H | H | H | cyclopropyl | 2-Cl-4-Cl | | |
| 506 | H | Me | H | H | H | cyclopropyl | 4-CF3 | | |
| 507 | H | Me | H | H | H | cyclopropyl | 4-OPh | | |

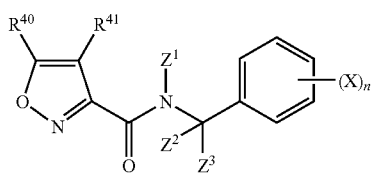

I-A¹⁵

| N° | R⁴⁰ | R⁴¹ | Z² | Z³ | Z¹ | (X)ₙ | LogP | M + H |
|---|---|---|---|---|---|---|---|---|
| 508 | Me | H | H | H | cyclopropyl | 2-Cl-4-Cl | | 325 |
| 509 | Me | H | H | H | cyclopropyl | 2-Cl-4-CF3 | | |
| 510 | Me | H | H | H | cyclopropyl | 2-Cl-4-Cl-6-Cl | | 359 |

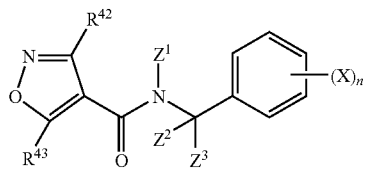

I-A¹⁶

| N° | R⁴² | R⁴³ | Z² | Z³ | Z¹ | (X)ₙ | LogP | M + H |
|---|---|---|---|---|---|---|---|---|
| 511 | Me | Me | H | H | Cyclopropyl | 2-Cl-4-Cl | | 339 |
| 512 | Me | Me | H | H | Cyclopropyl | 2-Cl-4-CF3 | | |
| 513 | Me | Me | H | H | Cyclopropyl | 2-Cl-4-Cl-6-Cl | | 373 |
| 514 | Me | CF3 | H | H | Cyclopropyl | 2-Cl-4-Cl | | |
| 515 | Me | CF3 | H | H | Cyclopropyl | 2-Cl-4-CF3 | | |
| 516 | Me | CF3 | H | H | Cyclopropyl | 2-Cl-4-Cl-6-Cl | | |
| 517 | CF3 | Me | H | H | Cyclopropyl | 2-Cl-4-Cl | | |
| 518 | CF3 | Me | H | H | Cyclopropyl | 2-Cl-6-CF3 | | |
| 519 | CF3 | Me | H | H | Cyclopropyl | 2-Cl-4-Cl-6-Cl | | |
| 520 | Me | Me | Me | H | Cyclopropyl | 2-Cl-4-Cl | | 353 |

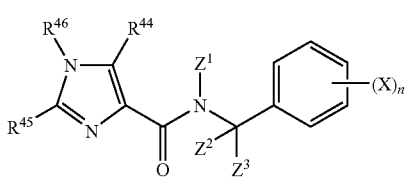

I-A¹⁷

| N° | R⁴⁴ | R⁴⁵ | R⁴⁶ | Z² | Z³ | Z¹ | (X)ₙ | LogP | M + H |
|---|---|---|---|---|---|---|---|---|---|
| 521 | H | H | Me | H | H | cyclopropyl | 2-Cl-4-Cl | | |
| 522 | H | H | Me | H | H | cyclopropyl | 2-Cl-4-CF3 | | |
| 523 | H | H | Me | H | H | cyclopropyl | 2-Cl-4-Cl-6-Cl | | |

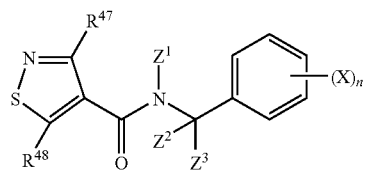

I-A¹⁸

| N° | R⁴⁷ | R⁴⁸ | Z² | Z³ | Z¹ | (X)ₙ | LogP | M + H |
|---|---|---|---|---|---|---|---|---|
| 524 | Me | NH2 | H | H | cyclopropyl | 2-Cl-4-Cl | | |
| 525 | Me | NH2 | H | H | cyclopropyl | 2-Cl-4-CF3 | | |
| 526 | Me | NH2 | H | H | cyclopropyl | 2-Cl-4-Cl-6-Cl | | |

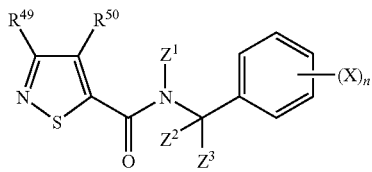

I-A¹⁹

| N° | R⁴⁹ | R⁵⁰ | Z² | Z³ | Z¹ | (X)ₙ | LogP | M + H |
|---|---|---|---|---|---|---|---|---|
| 527 | Cl | Cl | H | H | Cyclopropyl | 2-Cl-4-Cl | | 395 |
| 528 | Cl | Cl | H | H | Cyclopropyl | 2-Cl-4-CF3 | | |
| 529 | Cl | Cl | H | H | Cyclopropyl | 2-Cl-4-Cl-6-Cl | | 429 |
| 530 | Cl | Cl | H | H | 3,5,5-trimethyl-cyclohexyl | 2-Cl-4-Cl-6-Cl | | |
| 531 | Cl | Cl | H | H | cycloheptyl | 2-Cl-4-Cl-6-Cl | | |
| 532 | Cl | Cl | Me | H | Cyclopropyl | 2-Cl-4-Cl | | 409 |
| 533 | H | H | H | H | Cyclopropyl | 2-Cl-4-Cl-6-Cl | | 345 |
| 534 | H | H | H | H | Cyclopropyl | 2-Cl-4-Cl | | 311 |
| 535 | H | H | Me | H | Cyclopropyl | 2-Cl-4-Cl | | 325 |

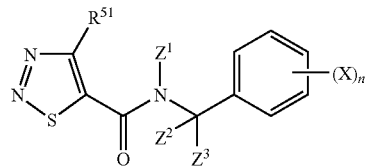

I-A²⁰

| N° | R⁵¹ | Z² | Z³ | Z¹ | (X)ₙ | LogP | M + H |
|---|---|---|---|---|---|---|---|
| 536 | Me | H | H | cyclopropyl | 2-Cl-4-Cl | | |
| 537 | Me | H | H | cyclopropyl | 2-Cl-4-CF3 | | |
| 538 | Me | H | H | cyclopropyl | 2-Cl-4-Cl-6-Cl | | |

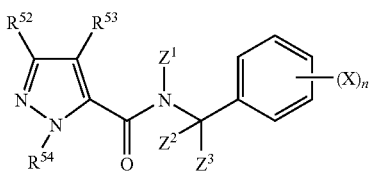

I-A²¹

| N° | R⁵² | R⁵³ | R⁵⁴ | Z² | Z³ | Z¹ | (X)ₙ | LogP | M + H |
|---|---|---|---|---|---|---|---|---|---|
| 539 | Me | Br | Et | H | H | cyclopropyl | 2-Cl-4-Cl | | |
| 540 | Me | Br | Et | H | H | cyclopropyl | 2-Cl-4-CF3 | | |
| 541 | Me | Br | Et | H | H | cyclopropyl | 2-Cl-4-Cl-6-Cl | 2.4 | |

I-A²²

| N° | R⁵⁵ | R⁵⁶ | R⁵⁷ | Z² | Z³ | Z¹ | (X)ₙ | LogP | M+H |
|---|---|---|---|---|---|---|---|---|---|
| 542 | H | H | Me | H | H | cyclopropyl | 2-Cl-4-Cl | | |
| 543 | H | H | Me | H | H | cyclopropyl | 2-Cl-4-CF3 | | |
| 544 | H | H | Me | H | H | cyclopropyl | 2-Cl-4-Cl-6-Cl | | |

The following examples illustrate in a non-limiting manner the preparation and efficacy of the compounds of formula (I) according to the invention.

PREPARATION EXAMPLE

N-(4-trifluoromethyl-benzyl)-N-cyclopropyl-5-fluoro-1,3-dimethyl-1H-pyrazole-4-carboxamide (compound 237)

A solution of 0.25 g (0.99 mmol) of N-(4-trifluoromethyl-benzyl)cyclopropylamine hydrochloride, 0.17 g (0.99 mmol) of 5-fluoro-1,3-dimethyl-1H-pyrazole-4-carbonyl chloride and 0.2 g (1.9 mmol) of triethylamine in THF (10 ml) is stirred at room temperature for 3 hours.

Solvent is removed under reduced pressure. Residue is partitioned between water and ethylacetate. Organic phase is separated, dried over magnesium sulfate and solvent evaporated. The resulting viscous oil was purified by flash chromatography using 1:1 heptane/ethyl acetate as eluent to yield 0.31 g of desired N-(4-trifluoromethyl-benzyl)-N-cyclopropyl-5-fluoro-1,3-dimethyl-1H-pyrazole-4-carboxamide as a white solid (Log P=2.8).

EFFICACY EXAMPLE A

In Vivo Preventive Test on *Alternia brassicae* (Leaf Spot of Crucifers)

The active ingredients tested are prepared by homogenization in a mixture of acetone/tween/DMSO, and then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the active ingredient prepared as described above.

Plants, used as controls, are treated with the mixture of acetone/tween/DMSO/water not containing the active material.

After 24 hours, the plants are contaminated by spraying them with an aqueous suspension of *Alternia brassicae* spores (40,000 spores per cm3). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good (at least 70%) or total protection is observed at a dose of 500 ppm with the following compounds: 27, 58, 59, 99, 100, 137, 160, 173, 187, 238, 243, 245, 246, 251, 255, 256, 258, 263, 264, 266, 274, 275, 301, 303, 308, 310, 322, 324, 328, 329, 351, 352, 353, 354, 373, 380, 386, 387, 389, 390, 395, 397, 400, 420, 421, 422, 423, 431, 432, 433, 438, 439, 452, 478, 479, 480, 481, 484, 486 and 534.

EFFICACY EXAMPLE B

In Vivo Preventive Test on *Pyrenophora teres* (Barley Net Blotch)

The active ingredients tested are prepared by homogenization in a mixture of acetone/tween/DMSO, then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) or total protection is observed at a dose of 500 ppm with the following compounds: 16, 24, 25, 27, 40, 41, 51, 65, 77, 87, 88, 94, 97, 100, 110, 113, 114, 116, 117, 128, 144, 168, 171, 172, 173, 178, 181, 187, 190, 196, 208, 209, 235, 236, 237, 238, 239, 240, 241, 242, 243, 245, 246, 248, 256, 258, 260, 262, 263, 264, 266, 274, 275, 276, 286, 298, 301, 302, 303, 307, 308, 310, 312, 313, 319, 324, 329, 351, 352, 353, 354, 355, 356, 357, 358, 379, 380, 387, 388, 390, 395, 397, 400, 404, 414, 415, 420, 421, 422, 423, 424, 431, 432, 433, 443, 463, 473, 478, 479, 480, 481 and 484.

EFFICACY EXAMPLE C

In Vivo Preventive Test on *Sphaerotheca fuliginea* (Cucurbit Powdery Mildew)

The active ingredients tested are prepared by homogenization in a mixture of acetone/tween/DMSO, then diluted with water to obtain the desired active material concentration.

Gherkin plants (Vert petit de Pans variety) in starter cups, sown on a 50/50 peat soil-pozzolana substrate and grown at 20° C./23° C., are treated at the 2-leaves stage by spraying with the aqueous suspension described above Plants, used as controls, are treated with the mixture of acetone/tween/DMSO/water not containing the active material.

After 24 hours, the plants are contaminated by spraying them with an aqueous suspension of *Sphaerotheca fuliginea* spores (100,000 spores per ml). The spores are collected from a contaminated plants. The contaminated gherkin plants are incubated at about 20° C./25° C. and at 60/70% relative humidity.

Grading (% of efficacy) is carried out 21 days after the contamination, in comparison with the control plants.

Under these conditions, good (at least 70%) or total protection is observed at a dose of 500 ppm with the following compounds: 24, 27, 35, 83, 87, 97, 98, 99, 100, 103, 105, 113, 114, 117, 124, 128, 130, 137, 144, 158, 160, 168, 169, 172, 173, 178, 209, 211, 212, 213, 228, 235, 238, 240, 243, 245, 246, 247, 248, 251, 252, 254, 255, 256, 258, 260, 264, 265, 266, 268, 275, 276, 280, 285, 287, 298, 299, 300, 301, 302, 305, 307, 309, 310, 312, 313, 319, 322, 323, 324, 328, 329, 338, 346, 351, 352, 353, 354, 355, 356, 357, 358, 372, 374, 375, 376, 379, 380, 382, 383, 385, 386, 387, 388, 389, 390, 391, 395, 397, 404, 414, 415, 420, 421, 423, 424, 434, 435, 436, 437, 438, 439, 440, 443, 445, 446, 449, 452, 460, 463, 468, 478, 479, 480, 481, 484, 486 and 490.

EFFICACY EXAMPLE D

In Vivo Preventive Test on *Mycosphaerella graminicola* (Wheat Leaf Spot)

The active ingredients tested are prepared by homogenization in a mixture of acetone/tween/DMSO, and then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the active ingredient prepared as described above.

Plants, used as controls, are treated with the mixture of acetone/tween/DMSO/water not containing the active material.

After 24 hours, the plants are contaminated by spraying them with an aqueous suspension of *Mycosphaerella graminicola* spores (500,000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 5, 13, 14, 16, 20, 24, 27, 35, 39, 41, 49, 54, 56, 58, 65, 77, 81, 84, 87, 88, 97, 99, 100, 101, 103, 104, 105, 106, 108, 109, 110, 111, 112, 113, 114, 117, 118, 121, 128, 133, 137, 141, 144, 150, 154, 158, 160, 171, 173, 176, 178, 180, 183, 187, 194, 196, 205, 209, 211, 212, 213, 228, 235, 236, 237, 238, 239, 240, 241, 242, 243, 244, 245, 246, 247, 248, 250, 256, 257, 258, 259, 260, 261, 263, 271, 274, 275, 276, 280, 282, 283, 285, 286, 287, 289, 295, 297, 298, 299, 300, 301, 303, 304, 305, 306, 308, 310, 312, 313, 319, 322, 323, 324, 328, 329, 332, 333, 335, 337, 338, 346, 347, 351, 352, 353, 354, 355, 356, 357, 358, 372, 374, 375, 376, 379, 383, 386, 387, 388, 389, 390, 391, 395, 397, 400, 404, 410, 415, 420, 421, 422, 423, 424, 426, 427, 433, 434, 435, 436, 437, 438, 439, 443, 445, 446, 460, 463, 464, 465, 466, 468, 473, 478, 479, 480, 481, 484, 486, 488, 489, 490, 492, 508, 511, 513, 520, 529, 532 and 535.

The invention claimed is:
1. A compound of formula (I)

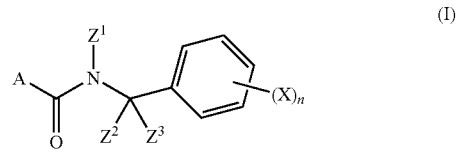

wherein
A represents a carbo-linked, unsaturated, 5-membered heterocyclyl group that can be substituted by up to four groups R;
$Z^1$ represents a non substituted $C_3$-$C_7$-cycloalkyl or a $C_3$-$C_7$ cycloalkyl substituted by up to 10 atoms or groups which can be the same or different and which can be selected from the group consisting of halogen atoms; cyano; $C_1$-$C_8$-alkyl; $C_1$-$C_8$-halogenoalkyl comprising up to 9 halogen atoms which can be the same or different; $C_1$-$C_8$-alkoxy; $C_1$-$C_8$-halogenoalkoxy comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl and di-$C_1$-$C_8$-alkylaminocarbonyl;
$Z^2$ and $Z^3$, which can be the same or different, represent a hydrogen atom; $C_1$-$C_8$-alkyl; $C_2$-$C_8$-alkenyl; $C_2$-$C_8$-alkynyl; cyano; nitro; a halogen atom; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbamoyl; di-$C_1$-$C_8$-alkylcarbamoyl; N—$C_1$-$C_8$-alkyl-$C_1$-$C_8$-alkoxycarbamoyl; or
$Z^2$ and $Z^3$ together with the carbon atom to which they are linked can form a substituted or non substituted $C_3$-$C_7$ cycloalkyl;
X, which can be the same or different, represents a halogen atom; nitro; cyano; hydroxyl; sulfanyl; amino; pentafluoro-λ6-sulfanyl; $C_1$-$C_8$-alkyl; $C_1$-$C_8$-halogenoalkyl comprising up to 9 halogen atoms which can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; $C_1$-$C_8$-alkylsulfanyl; $C_1$-$C_8$-halogenoalkylsulfanyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different $C_2$-$C_8$-alkenyloxy; $C_2$-$C_8$-halogenoalkenyloxy comprising up to 9 halogen atoms which can be the same or different; $C_2$-$C_8$-alkinyloxy; $C_2$-$C_8$-halogenoalkinyloxy comprising up to 9 halogen atoms which can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms which can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms which can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$- alkoxycarbamoyl; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl; $C_1$-$C_8$-alkylcarbonyloxy; $C_1$-$C_8$-halogenoalkylcarbonyloxy comprising up to 9 halogen atoms which can be the same or different; $C_1$-$C_8$-alkylcarbonylamino; $C_1$-$C_8$-halogenoalkylcarbonylamino comprising up to 9 halogen atoms which can be the same or different; $C_1$-$C_8$-alkylaminocarbonyloxy; alkylaminocarbonyloxy $C_1$-$C_8$-alkyloxycarbonyloxy, alkylsulphenyl, $C_1$-$C_8$-halogenoalkylsulphenyl comprising up to 9 halogen atoms which can be the same or different, $C_1$-$C_8$-alkylsulphinyl, $C_1$-$C_8$-halogenoalkylsulphinyl comprising up to 9 halogen atoms which can be the same or different, $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; naphthyl which can be substituted by up to 6 groups Q; phenoxy which can be substituted by up to 5 groups Q; phenylamino which can be substituted by up to 5 groups Q; phenylsulfanyl which can be substituted by up to 5 groups Q; phenylmethylene which can be substituted by up to 5 groups Q; pyridinyl which can be substituted by up to four groups Q and pyridinyloxy which can be substituted by up to four groups Q;

two substituents X together with the consecutive carbon atoms to which they are linked can form a 5- or 6-membered, saturated, carbo- or hetero-cycle, which can be substituted by up to four groups Q which can be the same or different;

n represents 1, 2, 3, 4 or 5;

R, which can be the same or different, represent hydrogen atom; halogen atom; cyano; nitro; amino; sulfanyl; pentafluoro-λ-6-sulfanyl; $C_1$-$C_8$-alkylamino; di-$C_1$-$C_8$-alkylamino; tri($C_1$-$C_8$-alkyl)silyl; $C_1$-$C_8$-alkylsulfanyl; $C_1$-$C_8$-halogenoalkylsulfanyl comprising up to 9 halogen atoms which can be the same or different; $C_1$-$C_8$-alkyl; $C_1$-$C_8$-halogenoalkyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different; $C_1$-$C_8$-alkoxy; $C_1$-$C_8$-halogenoalkoxy comprising up to 9 halogen atoms which can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$-alkylsulphinyl; $C_1$-$C_8$-alkylsulphonyl; $C_1$-$C_8$alkoxyimino; ($C_1$-$C_8$-alkoxyimino)-$C_1$-$C_8$-alkyl; (benzyloxyimino)-$C_1$-$C_8$-alkyl; phenoxy; benzyloxy; benzylsulfanyl; benzylamino; naphtyl; halogenophenoxy comprising up to 9 halogen atoms which can be the same or different; $C_1$-$C_8$-alkylcarbonyl; $C_1$-$C_8$-halogenoalkylcarbonyl comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl;

Q, which can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$) alkylsilyl and tri($C_1$-$C_8$)alkylsilyl-$C_1$-$C_8$-alkyl;

as well as salts, N-oxydes, metallic complexes, metalloidic complexes and optically active or geometric isomers thereof; with the exception of 2-furancarboxamide, N-(1,3-benzodioxol-5-ylmethyl)-N-cyclopentyl-5-methyl and 2-furancarboxamide, N-(1,3-benzodioxol-5-ylmethyl)-N-cyclopentyl-2,5-dimethyl.

2. A compound according to claim 1 wherein A is selected in the list consisting of:

a heterocycle of formula ($A^1$)

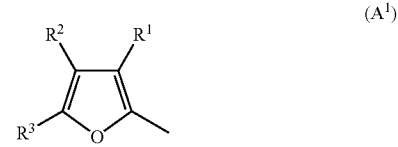

($A^1$)

wherein:
$R^1$ to $R^3$ which can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;

a heterocycle of formula ($A^2$)

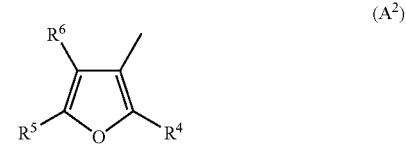

($A^2$)

wherein:
$R^4$ to $R^6$ which can be the same or different represent a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;

a heterocycle of formula ($A^3$)

($A^3$)

wherein:
$R^7$ represents a hydrogen atom; a halogen atom; $C_1$-$C_5$-alkyl; $C_1$-$C_5$-halogenoalkyl comprising up to 9 halogen atoms which can be the same or different; $C_1$-$C_5$-alkoxy or $C_1$-$C_5$-halogenoalkoxy comprising up to 9 halogen atoms which can be the same or different;

$R^8$ represents a hydrogen atom or a $C_1$-$C_5$-alkyl;
a heterocycle of formula ($A^4$)

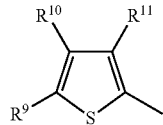

($A^4$)

wherein:
$R^9$ to $R^{11}$ which can be the same or different represent a hydrogen atom; a halogen atom; $C_1$-$C_5$-alkyl; amino; $C_1$-$C_5$-alkoxy; $C_1$-$C_5$-alkylthio $C_1$-$C_5$-halogenoalkyl comprising up to 9 halogen atoms which can be the same or different or $C_1$-$C_5$-halogenoalkoxy comprising up to 9 halogen atoms which can be the same or different;
a heterocycle of formula ($A^5$)

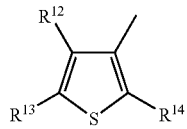

($A^5$)

wherein:
$R^{12}$ and $R^{13}$ which can be the same or different represent a hydrogen atom; a halogen atom; $C_1$-$C_5$-alkyl; $C_1$-$C_5$-alkoxy; amino; $C_1$-$C_5$-halogenoalkyl comprising up to 9 halogen atoms which can be the same or different or $C_1$-$C_5$-halogenoalkoxy comprising up to 9 halogen atoms which can be the same or different;
$R^{14}$ represents a hydrogen atom; a halogen atom; $C_1$-$C_5$-alkyl; $C_1$-$C_5$-alkoxy; amino; $C_1$-$C_5$-halogenoalkyl comprising up to 9 halogen atoms which can be the same or different or $C_1$-$C_5$-halogenoalkoxy comprising up to 9 halogen atoms which can be the same or different;
a heterocycle of formula ($A^6$)

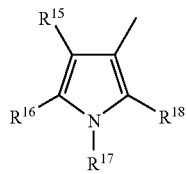

($A^6$)

wherein:
$R^{15}$ represents a hydrogen atom; a halogen atom; a cyano; $C_1$-$C_5$-alkyl; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;
$R^{16}$ and $R^{18}$ which can be the same or different represent a hydrogen atom; a halogen atom; $C_1$-$C_5$-alkoxycarbonyl; $C_1$-$C_5$-alkyl; $C_1$-$C_5$-halogenoalkoxy comprising up to 9 halogen atoms which can be the same or different or $C_1$-$C_5$-halogenoalkyl comprising up to 9 halogen atoms which can be the same or different;
$R^{17}$ represent a hydrogen atom or $C_1$-$C_5$-alkyl;
a heterocycle of formula ($A^7$)

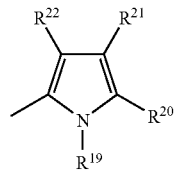

($A^7$)

wherein:
$R^{19}$ represents a hydrogen atom or a $C_1$-$C_5$-alkyl;
$R^{20}$ to $R^{22}$ which can be the same or different represent a hydrogen atom; a halogen atom; $C_1$-$C_5$-alkyl or $C_1$-$C_5$-halogenoalkyl comprising up to 9 halogen atoms which can be the same or different;
a heterocycle of formula ($A^8$)

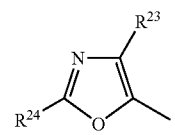

($A^8$)

wherein:
$R^{23}$ represents a hydrogen atom; a halogen atom; $C_1$-$C_5$-alkyl or $C_1$-$C_5$-halogenoalkyl comprising up to 9 halogen atoms which can be the same or different;
$R^{24}$ represents a hydrogen atom or $C_1$-$C_5$-alkyl or $C_1$-$C_5$-halogenoalkyl comprising up to 9 halogen atoms which can be the same or different;
a heterocycle of formula ($A^9$)

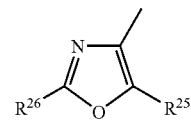

($A^9$)

wherein:
$R^{25}$ represents a hydrogen atom; a halogen atom; $C_1$-$C_5$-alkyl or $C_1$-$C_5$-halogenoalkyl comprising up to 9 halogen atoms which can be the same or different;
$R^{26}$ represents a hydrogen atom; $C_1$-$C_5$-alkyl or $C_1$-$C_5$-halogenoalkyl comprising up to 9 halogen atoms which can be the same or different;
a heterocycle of formula ($A^{10}$)

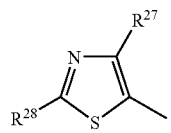

($A^{10}$)

wherein:
$R^{27}$ represents a hydrogen atom; a halogen atom; $C_1$-$C_5$-alkyl or $C_1$-$C_5$-halogenoalkyl comprising up to 9 halogen atoms which can be the same or different;
$R^{28}$ represents a hydrogen atom; a halogen atom; amino; $C_1$-$C_5$-alkyl or $C_1$-$C_5$-halogenoalkyl comprising up to 9 halogen atoms which can be the same or different;

a heterocycle of formula $(A^{11})$

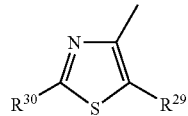

wherein:
- $R^{29}$ represents a hydrogen atom; a halogen atom; $C_1$-$C_5$-alkyl; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;
- $R^{30}$ represents a hydrogen atom; a bromine atom; a fluorine atom; an iodine atom; $C_1$-$C_5$-alkyl; $C_1$-$C_5$-halogenoalkyl comprising up to 9 halogen atoms which can be the same or different; $C_1$-$C_5$-halogenoalkoxy comprising up to 9 halogen atoms which can be the same or different; amino; $C_1$-$C_5$-alkylamino or di-$C_1$-$C_5$-alkylamino;

a heterocycle of formula $(A^{12})$

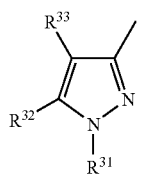

wherein:
- $R^{31}$ represents a hydrogen atom; a halogen atom or a $C_1$-$C_5$-alkyl;
- $R^{32}$ represents a hydrogen atom; a halogen atom; $C_1$-$C_5$-alkyl or $C_1$-$C_5$-halogenoalkyl comprising up to 9 halogen atoms which can be the same or different;
- $R^{33}$ represents a hydrogen atom; a halogen atom; a nitro; $C_1$-$C_5$-alkyl; $C_1$-$C_5$-alkoxy; $C_1$-$C_5$-halogenoalkoxy comprising up to 9 halogen atoms which can be the same or different or $C_1$-$C_5$-halogenoalkyl comprising up to 9 halogen atoms which can be the same or different;

a heterocycle of formula $(A^{13})$

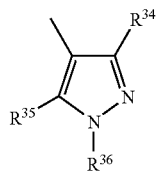

wherein:
- $R^{34}$ represents a hydrogen atom; a halogen atom; $C_1$-$C_5$-alkyl; $C_3$-$C_5$-cycloalkyl; $C_1$-$C_5$-halogenoalkyl comprising up to 9 halogen atoms which can be the same or different; $C_1$-$C_5$-alkoxy; $C_2$-$C_5$-alkynyloxy or $C_1$-$C_5$-halogenoalkoxy comprising up to 9 halogen atoms which can be the same or different;
- $R^{35}$ represents a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 9 halogen atoms which can be the same or different; $C_1$-$C_5$-halogenoalkoxy comprising up to 9 halogen atoms which can be the same or different; amino; $C_1$-$C_5$-alkylamino or di($C_1$-$C_5$-alkyl)amino;
- $R^{36}$ represents a hydrogen atom or $C_1$-$C_5$-alkyl;

a heterocycle of formula $(A^{14})$

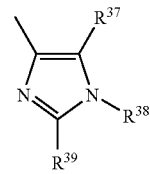

wherein:
- $R^{37}$ and $R^{39}$ which can be the same or different represent a hydrogen atom; a halogen atom; $C_1$-$C_5$-alkyl or $C_1$-$C_5$-halogenoalkyl comprising up to 9 halogen atoms which can be the same or different;
- $R^{38}$ represents a hydrogen atom or $C_1$-$C_5$-alkyl;

a heterocycle of formula $(A^{15})$

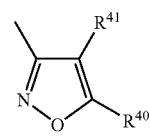

wherein:
- $R^{40}$ and $R^{41}$ which can be the same or different represent a hydrogen atom; a halogen atom; $C_1$-$C_5$-alkyl or $C_1$-$C_5$-halogenoalkyl comprising up to 9 halogen atoms which can be the same or different;

a heterocycle of formula $(A^{16})$

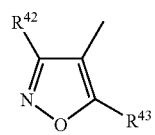

wherein:
- $R^{42}$ and $R^{43}$ which can be the same or different represent a hydrogen atom; a halogen atom; $C_1$-$C_5$-alkyl; $C_1$-$C_5$-halogenoalkyl comprising up to 9 halogen atoms which can be the same or different or amino;

a heterocycle of formula $(A^{17})$

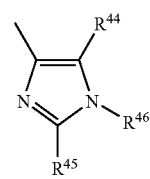

wherein:
- $R^{44}$ and $R^{45}$ which can be the same or different represent a hydrogen atom; a halogen atom; $C_1$-$C_5$-alkyl or $C_1$-$C_5$- halogenoalkyl comprising up to 9 halogen atoms which can be the same or different;
R$^{46}$ represents a hydrogen atom or C$_1$-C$_5$-alkyl;
a heterocycle of formula (A$^{18}$)

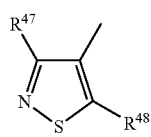

(A$^{18}$)

wherein:
R$^{47}$ represents a hydrogen atom; a halogen atom; C$_1$-C$_5$-alkyl or C$_1$-C$_5$-halogenoalkyl comprising up to 9 halogen atoms which can be the same or different;
R$^{48}$ represents a hydrogen atom; a halogen atom; C$_1$-C$_5$-alkyl; C$_1$-C$_5$-halogenoalkyl comprising up to 9 halogen atoms which can be the same or different or C$_1$-C$_5$-alkylsulfanyl;
a heterocycle of formula (A$^{19}$)

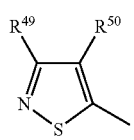

(A$^{19}$)

wherein:
R$^{49}$ and R$^{50}$ which can be the same or different represent a hydrogen atom; a halogen atom; C$_1$-C$_5$-alkyl; C$_1$-C$_5$-alkoxy; C$_1$-C$_5$-halogenoalkoxy comprising up to 9 halogen atoms which can be the same or different or C$_1$-C$_5$-halogenoalkyl comprising up to 9 halogen atoms which can be the same or different;
a heterocycle of formula (A$^{20}$)

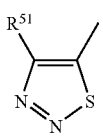

(A$^{20}$)

wherein:
R$^{51}$ represents a hydrogen atom; a halogen atom; C$_1$-C$_5$-alkyl or C$_1$-C$_5$-halogenoalkyl comprising up to 9 halogen atoms which can be the same or different;
a heterocycle of formula (A$^{21}$)

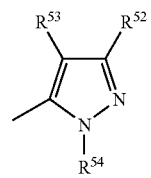

(A$^{21}$)

wherein:
R$^{52}$ and R$^{53}$ which can be the same or different represent a hydrogen atom; a halogen atom; C$_1$-C$_5$-alkyl; C$_1$-C$_5$- halogenoalkyl comprising up to 9 halogen atoms which can be the same or different; C$_1$-C$_5$-alkoxy or a C$_1$-C$_5$-alkylthio;
R$^{54}$ represents a hydrogen atom or C$_1$-C$_5$-alkyl;
a heterocycle of formula (A$^{22}$)

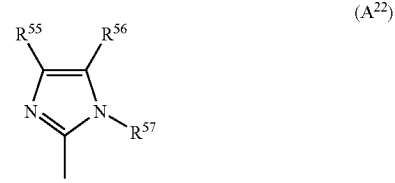

(A$^{22}$)

wherein:
R$^{55}$ and R$^{56}$ which can be the same or different represent a hydrogen atom; a halogen atom; C$_1$-C$_5$-alkyl or C$_1$-C$_5$-halogenoalkyl comprising up to 9 halogen atoms which can be the same or different;
R$^{57}$ represents a hydrogen atom or C$_1$-C$_5$-alkyl.

3. A compound according to claim 2 wherein A is selected in the list consisting of A$^2$; A$^6$; A$^{10}$ and A$^{13}$.

4. A compound according to claim 3 wherein A is A$^{13}$, and R$^{34}$ represents C$_1$-C$_5$-alkyl C$_1$-C$_5$-halogenoalkyl comprising up to 9 halogen atoms which can be the same or different; R$^{35}$ represents a hydrogen or a fluorine atom; R$^{36}$ represents methyl.

5. A compound according to claim 1 wherein Z$^1$ represents a non substituted C$_3$-C$_7$-cycloalkyl.

6. A compound according to claim 1 wherein Z$^1$ represents cyclopropyl.

7. A compound according to claim 1 wherein Z$^1$ represents a C$_3$-C$_7$ cycloalkyl substituted by up to 10 groups or atoms which can be the same or different and which can be selected ion in the list consisting of halogen atoms; C$_1$-C$_8$-alkyl; C$_1$-C$_8$-halogenoalkyl comprising up to 9 halogen atoms which can be the same or different; C$_1$-C$_8$-alkoxy or C$_1$-C$_8$-halogenoalkoxy comprising up to 9 halogen atoms which can be the same or different.

8. A compound according to claim 1 wherein X, which can be the same or different, represents a halogen atom; C$_1$-C$_8$-alkyl; C$_1$-C$_8$-halogenoalkyl comprising up to 9 halogen atoms which can be the same or different; C$_1$-C$_8$-alkoxy or C$_1$-C$_8$-halogenoalkoxy comprising up to 9 halogen atoms which can be the same or different.

9. A compound according to claim 1 wherein two consecutive substituents X together with the phenyl ring form a substituted or non substituted 1,3-benzodioxolyl; 1,2,3,4-tetrahydro-quinoxalinyl; 3,4-dihydro-2H-1,4-benzoxazinyl; 1,4-benzodioxanyl; indanyl; 2,3-dihydrobenzofuranyl; indolinyl.

10. A compound according to claim 1 wherein R which can be the same or different, represents a hydrogen atom; halogen atom; cyano; C$_1$-C$_8$-alkylamino; di-C$_1$-C$_8$-alkylamino; tri (C$_1$-C$_8$-alkyl)silyl; C$_1$-C$_8$-alkyl; C$_1$-C$_8$-halogenoalkyl comprising up to 9 halogen atoms which can be the same or different; C$_1$-C$_8$-alkoxy; C$_1$-C$_8$-halogenoalkoxy comprising up to 9 halogen atoms which can be the same or different; C$_1$-C$_8$-alkylsulfanyl; amino, hydroxyl; nitro; C$_1$-C$_8$-alkoxycarbonyl; C$_2$-C$_8$-alkynyloxy.

11. A fungicide composition comprising, as an active ingredient, an effective amount of a compound of formula (I) according to claim 1 and an agriculturally acceptable support, carrier or filler.

12. A process for the preparation of a compound of formula (I) according to claim 1 according to the following scheme:

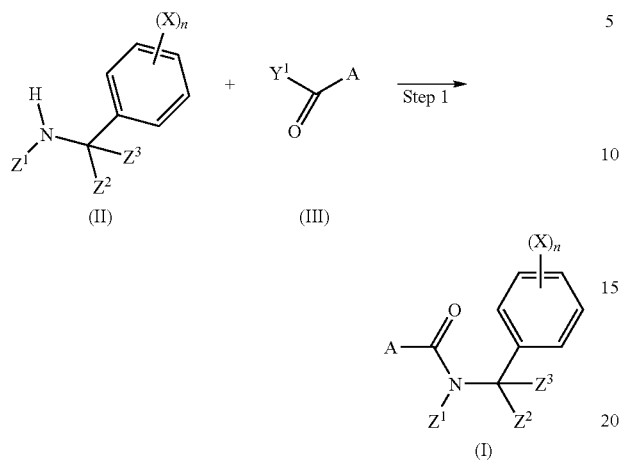

wherein

A represents a carbo-linked, unsaturated, 5-membered heterocyclyl group that can be substituted by up to four groups R;

$Z^1$ represents a non substituted $C_3$-$C_7$-cycloalkyl or a $C_3$-$C_7$ cycloalkyl substituted by up to 10 atoms or groups which can be the same or different and which can be selected from the group consisting of halogen atoms; cyano; $C_1$-$C_8$-halogenoalkyl comprising up to 9 halogen atoms which can be the same or different; $C_1$-$C_8$-alkoxy; $C_1$-$C_8$-halogenoalkoxy comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl and di-$C_1$-$C_8$-alkylaminocarbonyl;

$Z^2$ and $Z^3$, which can be the same or different, represent a hydrogen atom; $C_1$-$C_8$-alkyl; $C_2$-$C_8$-alkenyl; $C_2$-$C_8$-alkynyl; cyano; nitro; a halogen atom; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbamoyl; di-$C_1$-$C_8$-alkylcarbamoyl; N—$C_1$-$C_8$-alkyl-$C_1$-$C_8$-alkoxycarbamoyl; or $Z^2$ and $Z^3$ together with the carbon atom to which they are linked can form a substituted or non substituted $C_3$-$C_7$ cycloalkyl;

X, which can be the same or different, represents a halogen atom; nitro; cyano; hydroxyl; sulfanyl; amino; pentafluoro-λ6-sulfanyl; $C_1$-$C_8$-alkyl; $C_1$-$C_8$-halogenoalkyl comprising up to 9 halogen atoms which can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; $C_1$-$C_8$-alkylsulfanyl; $C_1$-$C_8$-halogenoalkylsulfanyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different; $C_2$-$C_8$-alkenyloxy; $C_2$-$C_8$-halogenoalkenyloxy comprising up to 9 halogen atoms which can be the same or different; $C_2$-$C_8$-alkynyloxy; $C_2$-$C_8$-halogenoalkynyloxy comprising up to 9 halogen atoms which can be the same or different; $C_3$-$C_7$-cycloalkyl; $C_3$-$C_7$cycloalkyl-$C_1$-$C_8$-alkyl; $C_3$-$C_7$-halogenocycloalkyl comprising up to 9 halogen atoms which can be the same or different; formyl; formyloxy; formylamino; carboxy carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms which can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl; $C_1$-$C_8$-alkylcarbonyloxy; $C_1$-$C_8$-halogenoalkylcarbonyloxy comprising up to 9 halogen atoms which can be the same or different; $C_1$-$C_8$-alkylcarbonylamino; $C_1$-$C_8$-halogenoalkylcarbonylamino comprising up to 9 halogen atoms which can be the same or different; $C_1$-$C_8$-alkylaminocarbonyloxy; di-$C_1$-$C_8$-alkylaminocarbonyloxy; $C_1$-$C_8$-alkyloxycarbonyloxy, $C_1$-$C_8$-alkylsulphenyl, $C_1$-$C_8$-halogenoalkylsulphenyl comprising up to 9 halogen atoms which can be the same or different, $C_1$-$C_8$-alkylsulphinyl, $C_1$-$C_8$-halogenoalkylsulphinyl comprising up to 9 halogen atoms which can be the same or different, $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; naphthyl which can be substituted by up to 6 groups Q; phenoxy which can be substituted by up to 5 groups Q; phenylamino which can be substituted by up to 5 groups Q; phenylsulfanyl which can be substituted by up to 5 groups Q; phenylmethylene which can be substituted by up to 5 groups Q; pyridinyl which can be substituted by up to four groups Q and pyridinyloxy which can be substituted by up to four groups Q;

two substituents X together with the consecutive carbon atoms to which they are linked can form a 5- or 6-membered, saturated, carbo- or hetero-cycle, which can be substituted by up to four groups Q which can be the same or different;

n represents 1, 2, 3, 4 or 5; and $Y^1$ represents a halogen or a hydroxyl.

13. A process for the preparation of a compound of formula (I) according to claim 1 according to the following scheme:

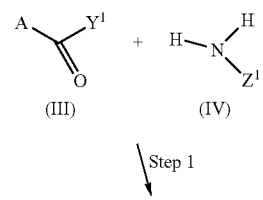

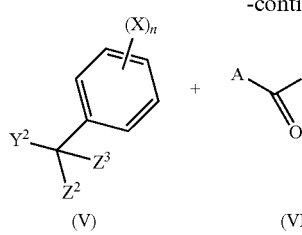
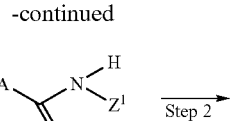
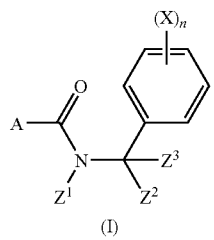

wherein;

A represents a carbo-linked, unsaturated, 5-membered heterocyclyl group that can be substituted by up to four groups R;

$Z^1$ represents a non substituted $C_3$-$C_7$-cycloalkyl or a $C_3$-$C_7$ cycloalkyl substituted by up to 10 atoms or groups which can be the same or different and which can be selected from the group consisting of halogen atoms; cyano; $C_1$-$C_8$-alkyl; $C_1$-$C_8$-halogenoalkyl comprising up to 9 halogen atoms which can be the same or different; $C_1$-$C_8$-alkoxy; $C_1$-$C_8$-halogenoalkoxy comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl and di-$C_1$-$C_8$-alkylaminocarbonyl;

$Z^2$ and $Z^3$, which can be the same or different, represent a hydrogen atom; $C_1$-$C_8$-alkyl; $C_2$-$C_8$-alkenyl; $C_2$-$C_8$-alkynyl; cyano; nitro; a halogen atom; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbamoyl; di-$C_1$-$C_8$-alkylcarbamoyl; alkyl-$C_1$-$C_8$-alkoxycarbamoyl; or $Z^2$ and $Z^3$ together with the carbon atom to which they are linked can form a substituted or non substituted $C_3$-$C_7$ cycloalkyl;

X, which can be the same or different, represents a halogen atom; nitro; cyano; hydroxyl; sulfanyl; amino; pentafluoro-λ6-sulfanyl; $C_1$-$C_8$-alkyl; $C_1$-$C_8$-halogenoalkyl comprising up to 9 halogen atoms which can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; $C_1$-$C_8$-alkylsulfanyl; $C_1$-$C_8$-halogenoalkylsulfanyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different $C_2$-$C_8$-alkenyloxy; $C_1$-$C_8$-halogenoalkenyloxy comprising up to 9 halogen atoms which can be the same or different; $C_2$-$C_8$-alkinyloxy; $C_2$-$C_8$-halogenoalkinyloxy comprising up to 9 halogen atoms which can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms which can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms which can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl N—$C_1$-$C_8$-alkyl-$C_1$-$C_8$-alkoxycarbamoyl; $C_1$-$C_8$-alkoxycarbonyl; halogenoalkoxycarbonyl comprising up to 9 halogen atoms which can be the same or different; $C_1$-$C_8$-alkylaminocarbonyl; di-$C_1$-$C_8$-alkylaminocarbonyl; $C_1$-$C_8$-alkylcarbonyloxy $C_1$-$C_8$-halogenoalkylcarbonyloxy comprising up to 9 halogen atoms which can be the same or different; $C_1$-$C_8$-alkylcarbonylamino; $C_1$-$C_8$-halogenoalkylcarbonylamino comprising up to 9 halogen atoms which can be the same or different; $C_1$-$C_8$-alkylaminocarbonyloxy; di-$C_1$-$C_8$-alkylaminocarbonyloxy; $C_1$-$C_8$-alkyloxycarbonyloxy, $C_1$-$C_8$-alkylsulphenyl, $C_1$-$C_8$-halogenoalkylsulphenyl comprising up to 9 halogen atoms which can be the same or different, $C_1$-$C_8$-alkylsulphinyl, $C_1$-$C_8$-halogenoalkylsulphinyl comprising up to 9 halogen atoms which can be the same or different, $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; naphthyl which can be substituted by up to 6 groups Q; phenoxy which can be substituted by up to 5 groups Q; phenylamino which can be substituted by up to 5 groups Q; phenylsulfanyl which can be substituted by up to 5 groups Q; phenylmethylene which can be substituted by up to 5 groups Q; pyridinyl which can be substituted by up to four groups Q and pyridinyloxy which can be substituted by up to four groups Q;

two substituents X together with the consecutive carbon atoms to which they are linked can form a 5- or 6-membered, saturated, carbo- or hetero-cycle, which can be substituted by up to four groups Q which can be the same or different;

n represents 1, 2, 3, 4 or 5;

$Y^1$ represents a halogen or a hydroxyl; and $Y^2$ represents a halogen or a leaving group like a tosylate group.

14. A process for the preparation of a compound of formula (I) according to claim 1 according to the following scheme:

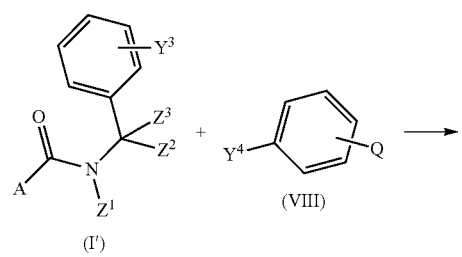

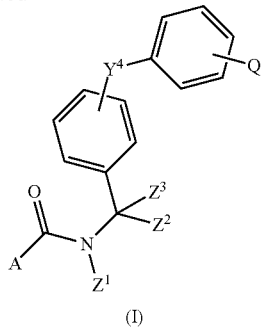

wherein

A represents a carbo-linked, unsaturated, 5-membered heterocyclyl group that can be substituted by up to four groups R;

$Z^1$ represents a non substituted $C_3$-$C_7$-cycloalkyl or a $C_3$-$C_7$ cycloalkyl substituted by up to 10 atoms or groups which can be the same or different and which can be selected from the group consisting of halogen atoms; cyano; $C_1$-$C_8$-alkyl; $C_1$-$C_8$-halogenoalkyl comprising up to 9 halogen atoms which can be the same or different; $C_1$-$C_8$-alkoxy; $C_1$-$C_8$-halogenoalkoxy comprising up to 9 halogen atoms which can be the same or different; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl and di-$C_1$-$C_8$-alkylaminocarbonyl;

$Z^2$ and $Z^3$, which can be the same or different, represent a hydrogen atom; $C_1$-$C_8$-alkyl; $C_2$-$C_8$-alkenyl; $C_2$-$C_8$-alkynyl; cyano; nitro; a halogen atom; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbamoyl; di-$C_1$-$C_8$-alkylcarbamoyl; N—$C_1$-$C_8$-alkyl-$C_1$-$C_8$-alkoxycarbamoyl; or $Z^2$ and $Z^3$ together with the carbon atom to which they are linked can form a substituted or non substituted $C_3$-$C_7$ cycloalkyl;

X, which can be the same or different, represents a halogen atom; nitro cyano; hydroxyl; sulfanyl; amino; pentafluoro-λ6-sulfanyl; $C_1$-$C_8$-alkyl; $C_1$-$C_8$-halogenoalkyl comprising up to 9 halogen atoms which can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; $C_1$-$C_8$-alkylsulfanyl; $C_1$-$C_8$-halogenoalkylsulfanyl comprising up to 9 halogen atoms which can be the same or different; $C_2$-$C_8$-alkenyl; $C_2$-$C_8$-halogenoalkenyl comprising up to 9 halogen atoms which can be the same or different; $C_2$-$C_8$-alkynyl; $C_2$-$C_8$-halogenoalkynyl comprising up to 9 halogen atoms which can be the same or different; $C_2$-$C_8$-alkenyloxy; $C_2$-$C_8$-halogenoalkenyloxy comprising up to 9 halogen atoms which can be the same or different; $C_2$-$C_8$-alkinyloxy; $C_2$-$C_8$-halogenoalkinyloxy comprising up to 9 halogen atoms which can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms which can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms which can be the same or different; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl comprising up to 9 halogen atoms which can be the same or different; $C_1$-$C_8$-alkylaminocarbonyl; di-$C_1$-$C_8$-alkylaminocarbonyl $C_1$-$C_8$-alkylcarbonyloxy; $C_1$-$C_8$-halogenoalkylcarbonyloxy comprising up to 9 halogen atoms which can be the same or different; $C_1$-$C_8$-alkylcarbonylamino; $C_1$-$C_8$-halogenoalkylcarbonylamino comprising up to 9 halogen atoms which can be the same or different; $C_1$-$C_8$-alkylaminocarbonyloxy; di-$C_1$-$C_8$-alkylaminocarbonyloxy; $C_1$-$C_8$-alkyloxycarbonyloxy, $C_1$-$C_8$-alkylsulphenyl, $C_1$-$C_8$-halogenoalkylsulphenyl comprising up to 9 halogen atoms which can be the same or different, $C_1$-$C_8$-alkylsulphinyl, $C_1$-$C_8$-halogenoalkylsulphinyl comprising up to 9 halogen atoms which can be the same or different; $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; naphthyl which can be substituted by up to 6 groups Q; phenoxy which can be substituted by up to 5 groups Q; phenylamino which can be substituted by up to 5 groups Q; phenylsulfanyl which can be substituted by up to 5 groups Q; phenylmethylene which can be substituted by up to 5 groups Q; pyridinyl which can be substituted by up to four groups Q and pyridinyloxy which can be substituted by up to four groups Q;

two substituents X together with the consecutive carbon atoms to which they are linked can form a 5- or 6-membered, saturated, carbo- or hetero-cycle, which can be substituted by up to four groups Q which can be the same or different;

n represents 1, 2, 3, 4 or 5;

Q, which can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$) alkylsilyl and tri($C_1$-$C_8$)alkylsilyl-$C_1$-$C_8$-alkyl;

$Y^3$ represents a halogen atom; and $Y^4$ represents sulphur, oxygen or $C_1$-$C_5$-alkylamino.

15. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

16. A method for controlling phytopathogenic fungi of crops, characterized in that an agronomically effective and substantially non-phytotoxic quantity of a composition according to claim 11 is applied to the soil where plants grow or are capable of growing, to the leaves and/or the fruit of plants or to the seeds of plants.

* * * * *